United States Patent
Reda et al.

(10) Patent No.: US 10,102,441 B2
(45) Date of Patent: Oct. 16, 2018

(54) METHODS FOR AUTOMATIC SEGMENTATION OF INNER EAR ANATOMY IN POST-IMPLANTATION CT AND APPLICATIONS OF SAME

(71) Applicant: Vanderbilt University, Nashville, TN (US)

(72) Inventors: Fitsum A. Reda, Nashville, TN (US); Jack H. Noble, Nashville, TN (US); Benoit Dawant, Nashville, TN (US); Robert F. Labadie, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 15/116,012

(22) PCT Filed: Jan. 30, 2015

(86) PCT No.: PCT/US2015/013899
§ 371 (c)(1),
(2) Date: Aug. 2, 2016

(87) PCT Pub. No.: WO2015/116994
PCT Pub. Date: Aug. 6, 2015

(65) Prior Publication Data
US 2017/0177967 A1    Jun. 22, 2017

Related U.S. Application Data
(63) Continuation of application No. PCT/US2014/015332, filed on Feb. 7, 2014.
(Continued)

(51) Int. Cl.
*G06K 9/00* (2006.01)
*G06K 9/34* (2006.01)
(Continued)

(52) U.S. Cl.
CPC ............. *G06K 9/34* (2013.01); *A61B 6/032* (2013.01); *A61B 6/12* (2013.01); *A61B 6/501* (2013.01);
(Continued)

(58) Field of Classification Search
CPC ... A61B 5/0066; A61B 5/1076; A61B 5/1077; A61B 5/6817; A61B 6/032; A61B 6/12;
(Continued)

(56) References Cited

U.S. PATENT DOCUMENTS 7,206,639 B2 *  4/2007  Jacobsen ............... A61F 11/00
                                                     607/57
8,135,453 B2    3/2012  Slabaugh et al.
(Continued)

FOREIGN PATENT DOCUMENTS

WO    2013152077 A1    10/2013

OTHER PUBLICATIONS

Noble, Jack H., Statistical Shape Model Segmentation and Frequency Mapping of Cochlear Implant Stimulation Targets in CT, Medical Image Computing and Computer-Assisted Interv, 2012, pp. 421-428.
(Continued)

*Primary Examiner* — Aklilu Woldemariam
(74) *Attorney, Agent, or Firm* — Locke Lord LLP; Tim Tingkang Xia, Esq.

(57) ABSTRACT

A method for automatic segmentation of intra-cochlear anatomy in post-implantation CT image of bilateral cochlear implant recipients includes coarsely segmenting a labyrinth with a labyrinth surface chosen from a library of inner ear anatomy shapes; creating a target specific ASM for each of the labyrinth and the SOIs using a set of inner ear anatomy surfaces selected from the library of inner ear anatomy shapes such that the set of inner ear anatomy surfaces has the
(Continued)

smallest dissimilarity quantity with the coarsely localized labyrinth surface in the post-implantation CT image; refining the coarsely segmented labyrinth surface by performing an ASM-based segmentation of the labyrinth using the target-specific ASM of the labyrinth to obtain a segmented labyrinth; and fitting the points of the target-specific ASM of the SOIs to their corresponding points on the segmented labyrinth to segment the SOIs in the post-implantation CT image.

42 Claims, 24 Drawing Sheets

Related U.S. Application Data

(60) Provisional application No. 61/935,022, filed on Feb. 3, 2014, provisional application No. 61/762,024, filed on Feb. 7, 2013, provisional application No. 61/837,028, filed on Jun. 19, 2013.

(51) Int. Cl.
| | |
|---|---|
| *A61B 6/03* | (2006.01) |
| *A61B 6/12* | (2006.01) |
| *A61B 6/00* | (2006.01) |
| *G06K 9/46* | (2006.01) |
| *G06K 9/62* | (2006.01) |
| *A61N 1/36* | (2006.01) |

(52) U.S. Cl.
CPC .......... *A61B 6/5211* (2013.01); *A61B 6/5235* (2013.01); *G06K 9/4671* (2013.01); *G06K 9/6215* (2013.01); *A61N 1/36038* (2017.08); *G06K 9/00* (2013.01); *G06K 2209/051* (2013.01)

(58) Field of Classification Search
CPC .. A61B 6/501; A61B 6/50; A61B 6/52; A61B 6/5211; A61B 6/5235; A61B 6/5294; A61B 10/02; A61B 10/0241; A61B 2010/0208; A61B 2090/395; A61B 34/25; A61B 5/0035; A61B 5/0059; A61B 6/00; A61B 6/508; A61B 6/5247; A61B 8/12; A61B 8/463; A61B 8/483; A61B 2034/104; A61B 2034/105; A61B 34/10; A61B 5/12; A61B 5/4893; A61B 6/03; A61B 6/042; G06T 2207/10072; G06T 2207/20076; G06T 2207/30004; G06T 7/33; G06T 7/66; G06T 2207/10081; G06T 2207/20124; G06T 2207/20128; G06T 2207/30052; G06T 7/12; G06T 7/149; G06T 7/30; G06T 7/337; G06T 2207/10; H04R 25/652; H04R 25/658; G06K 2209/051; G06K 9/34; G06K 9/4671; G06K 9/6215; A61N 1/36038; A61N 1/0541; A61N 1/36036; A61N 1/36032; A61N 1/361; A61N 1/36185; A61N 2005/005; A61N 2005/0605; A61N 2005/063; A61N 2005/0631; A61N 2005/0652; A61N 2005/0659; A61N 2005/0665; A61N 2005/00; A01K 1/031; A61F 11/00; A61K 9/0046; A61M 31/00
USPC ........ 382/128, 129, 130, 131, 132; 600/473, 600/443, 467, 476; 607/57
See application file for complete search history.

(56) References Cited

U.S. PATENT DOCUMENTS

| | | | |
|---|---|---|---|
| 2006/0264897 A1* | 11/2006 | Lobl ................. | A61M 39/0208 604/506 |
| 2009/0060308 A1 | 3/2009 | Dawant et al. | |
| 2009/0325938 A1* | 12/2009 | Lichter ............... | A61K 9/0046 514/220 |
| 2010/0022661 A1* | 1/2010 | Lichter ............... | A61K 9/0046 514/772.1 |
| 2011/0195123 A1* | 8/2011 | Shemi ................. | A61K 9/0024 424/484 |
| 2011/0288613 A1* | 11/2011 | Smith ................ | A61N 1/36032 607/57 |
| 2012/0191161 A1* | 7/2012 | van Dijk .............. | A61N 1/0541 607/57 |
| 2015/0018699 A1* | 1/2015 | Zeng .................. | A61B 5/04001 600/509 |
| 2015/0088225 A1* | 3/2015 | Noble ................ | A61N 1/36032 607/57 |
| 2015/0245817 A1* | 9/2015 | Stone .................... | A61B 90/39 600/443 |

OTHER PUBLICATIONS

Noble, Jack H., Automatic Segmentation of Intracochlear Anatomy in Conventional CT, IEEE Transactions on Biomedical Engineering, Sep. 2011, pp. 2625-2632, vol. 58, No. 9.

Korean Intellectual Property Office, "International Search Report for PCT/US2015/013899", KR, dated May 14, 2015.

Noble, J.H., Labadie, R.F., Gifford, R.H., Dawant, B.M., "Image-guidance enables new methods for customizing cochlear implant stimulation strategies," Neural Systems and Rehabilitation Engineering, IEEE Transactions on 21(5):820-829, Sep. 2013.

Noble, J.H., Labadie, R.F., Majdani, O., Dawant, B.M., "Automatic Segmentation of Intracochlear Anatomy in Conventional CT," Biomedical Engineering, IEEE Transactions on, 58(9):2625-2632, Sep. 2011.

Noble, J.H., Schuman, T.A., Wright, C.G., Labadie, R.F., Dawant, B.M., "Automatic identification of cochlear implant electrode arrays for post-operative assessment", Proc. SPIE 7962, Medical Imaging 2011: Image Processing, 796217.

Schuman, T.A., Noble, J.H., Wright, C.G., Wanna, G.B., Dawant, B.M., Labadie, R.F., "Anatomic Verification of a Novel, Non-rigid Registration Method for Precise Intrascalar Localization of Cochlear Implant Electrodes in Adult Human Temporal Bones Using Clinically-available Computerized Tomography," The Laryngoscope, 120 (11):2277-2283, 2010.

Wanna, G.B., Noble, J.H., McRackan, T.R., Dawant, B.M., Dietrich, M.S., Watkins, L.D., Rivas, A., Schuman, T.A., Labadie, R.F., "Assessment of electrode positions and audiological outcomes in bilateral cochlear implant patients," Otology & Neurotology, 32(3):428-432, 2011.

Noble, J.H., Gifford, R.H., Labadie, R.F., Dawant, B.M., "Statistical Shape Model Segmentation and Frequency Mapping ofCochlear Implant Stimulation Targets in CT," Medical Image Computing and Computer-Assisted Intervention—MICCAI 2012, 421-428, 2012.

Reda, F.A., Dawant, B.M., McRackan, T.R., Labadie, R.F., Noble, J.H., "Automatic segmentation of intra-cochlear anatomy in post-implantation CT", Proc. SPIE 8671, Medical Imaging 2013: Image-Guided Procedures, Robotic Interventions, and Modeling, 86710I.

Maes, F., Collignon, A., Vandermeulen, D., Mrchal, G., and Suetens, P., "Multimodality image registration by maximization of mutual information," IEEE Trans. Med. Imaging 16, 187-198 (1997).

Wells III, W.M., Viola, P., Atsumi, H., Nakajima, S., Kikinis, R., "Multi-modal volume registration by maximization of mutual information," Med. Image Anal. 1, 35-51 (1996).

Rohde, G.K., Aldroubi, A., Dawant, B.M., "The adaptive bases algorithm for intensity-based nonrigid image registration," IEEE Trans.Med. Imag., vol. 22, No. 11, pp. 1470-1479, Nov. 2003.

(56) References Cited

OTHER PUBLICATIONS

Cootes, T.F., Taylor, C.J., Cooper, D.H., Graham, J., "Active shape models—Their training and application," Comp. Vis. Image Understanding, vol. 61, No. 1, pp. 39-59, 1995.
Reda, F.A., McRackan, T. R., Labadie, R. F., Dawant, B. M., Noble, J.H., "Automatic segmentation of inner ear anatomy in post-implantation CT of unilateral cochlear implant recipients", Medical Image Analysis, 18(3):605-615, Apr. 2014.

* cited by examiner

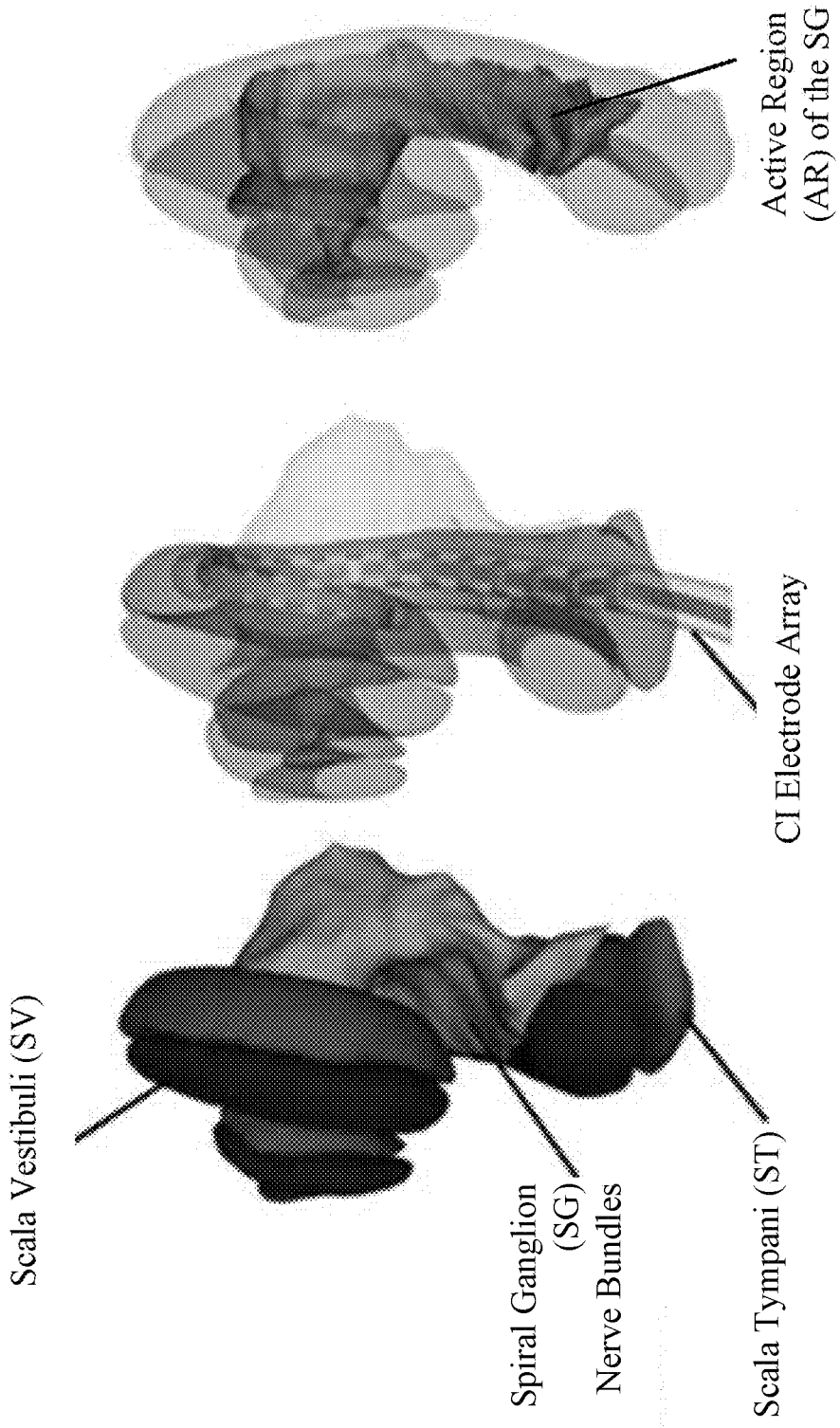

Post-implantation CT

Post-implantation CT

Pre-implantation CT 2.5 mm

Pre-implantation CT

Semi-circular canals

Vestibule of the ear

Semi-circular canals and vestibuli (SCCV)

The rest of the labyrinth

METHODS FOR AUTOMATIC SEGMENTATION OF INNER EAR ANATOMY IN POST-IMPLANTATION CT AND APPLICATIONS OF SAME

CROSS-REFERENCE TO RELATED PATENT APPLICATIONS

This application is a US national stage application of PCT Patent Application Serial No. PCT/US2015/013899, filed Jan. 30, 2015, entitled "METHODS FOR AUTOMATIC SEGMENTATION OF INNER EAR ANATOMY IN POST-IMPLANTATION CT AND APPLICATIONS OF SAME," by Fitsum A Reda et al., which itself claims priority to and the benefit of, pursuant to 35 U.S.C. § 119(e), U.S. Provisional Patent Application Ser. No. 61/935,022, filed Feb. 3, 2014, entitled "ALGORITHMS FOR AUTOMATIC SEGMENTATION OF THE INTERNAL STRUCTURES OF THE EAR IN POST-IMPLANTATION CT OF BILATERAL COCHLEAR IMPLANT RECIPIENTS AND APPLICATIONS OF SAME", by Fitsum A. Reda et al., each of which is incorporated herein in its entirety by reference.

This application is also a continuation-in-part application of PCT Application Serial No. PCT/US2014/015332, filed Feb. 7, 2014, entitled "AUTOMATIC SEGMENTATION OF INTRA-COCHLEAR ANATOMY IN POST-IMPLANTATION CT OF UNILATERAL COCHLEAR IMPLANT RECIPIENTS", by Fitsum A. Reda et al., which itself claims priority to and the benefit of, pursuant to 35 U.S.C. § 119(e), U.S. Provisional Patent Application Ser. No. 61/762,024, filed Feb. 7, 2013, entitled "METHOD FOR AUTOMATIC SEGMENTATION OF INTRA-COCHLEAR ANATOMY IN POST-IMPLANTATION CT", by Fitsum A. Reda et al., and U.S. Provisional Patent Application Ser. No. 61/837,028, filed Jun. 19, 2013, entitled "METHOD FOR AUTOMATIC SEGMENTATION OF INTRA-COCHLEAR ANATOMY IN POST-IMPLANTATION CT", by Fitsum A. Reda et al. Each of the above-identified applications is incorporated herein in its entirety by reference.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [8] represents the 8th reference cited in the reference list, namely, Reda, F. A., Dawant, B. M., McRackan, T. R., Labadie, R. F., Noble, J. H., "Automatic segmentation of intra-cochlear anatomy in post-implantation CT", Proc. SPIE 8671, Medical Imaging 2013: Image-Guided Procedures, Robotic Interventions, and Modeling, 86710I.

STATEMENT AS TO RIGHTS UNDER FEDERALLY-SPONSORED RESEARCH

This invention was made with government support under grant numbers R01DC008408, R21DC012620 and R01DC010184 awarded by the National Institute of Deafness and Other Communication Disorders. The government has certain rights in the invention.

FIELD OF THE INVENTION

The invention relates generally to cochlear implants, and more particularly, to shape library-based methods for automatic segmentation of inner ear anatomy in post-implantation CT of bilateral cochlear implant recipients and applications of the same.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

A cochlear implant (CI) is a device that restores hearing by directly stimulating the auditory nerve using an electrode array that is surgically placed in the cochlea. The CI device includes a sound processor component, typically worn behind the ear, which processes and converts sounds detected by a microphone into electrical signals sent to implanted electrodes. The CI sound processor is programmed by an audiologist who determines a number of processor programming parameters that specify the electrical signals sent to implanted electrodes to attempt to optimize hearing outcome. The number of electrodes in a CI electrode array range from 12 to 22, depending on the manufacturer.

We recently developed and are currently testing image-guided cochlear implant programming (IGCIP) strategies that rely on patient-specific knowledge of spatial relationship between implanted electrodes and inner ear structures. The inner ear structures-of-interest (SOIs) are the scala tympani (ST), the scala vestibuli (SV), and the spiral ganglion (SG). The ST and the SV are the two principal cavities of the cochlea. The SG is an anatomical region that contains the group of nerves targeted for stimulation by implanted electrodes. FIG. 1A shows surfaces of the ST, the SV and the SG of a representative subject. FIG. 1B shows an example surface model of an electrode array inserted into the cochlea, and FIG. 1C shows a surface of the active region (AR), which is the interface between the SG and the union of the ST and the SV. The AR is the region of nerves most likely to receive electrical stimulation from implanted electrodes.

The IGCIP strategies are enabled by a number of algorithms we have developed that permit determining the position of implanted electrodes relative to the SOIs using a pre- and a post-implantation CT [2-7]. In a preliminary study with over thirty CI recipients, we have shown that IGCIP strategies can significantly improve hearing outcomes [1]. One issue with the IGCIP strategies is that it does not extend to CI recipients for whom a pre-implantation CT is not available. This is because implant related image artifacts present in post-implantation CTs make it difficult to localize the SOIs in those images directly. Thus far, the SOIs have been first localized in a pre-implantation CT and then mapped onto a post-implantation CT, on which their positions relative to implanted electrodes are analyzed. Specifically, this approach, which we previously developed, includes three steps. First, we segment the SOIs in a pre-implantation CT. Next, we localize the electrodes in a corresponding post-implantation CT. Finally, we rigidly register the two CTs to determine the position of implanted electrodes relative to the SOIs. When subjects receive unilateral CIs, we have also developed approaches for determining electrodes position relative to SOIs using post-implantation CTs alone, without requiring a corresponding pre-implantation CT. This approach involves segmenting the SOIs in the implanted ear by mapping the SOI surfaces segmented from the contralateral normal ear [8, 14]. However, the approaches we developed so far cannot be used for many CI recipients for whom a pre-implantation CT of neither ear is available.

Therefore, a heretofore unaddressed need exists in the art to address the aforementioned deficiencies and inadequacies.

SUMMARY OF THE INVENTION

One of the objectives of the invention is to provide algorithms that extend the IGCIP strategies to the subpopulation of bilateral CI recipients for whom a pre-implantation CT is not available, thereby making the IGCIP strategies available for all CI recipients. The algorithms permit us to automatically segment the SOIs in post-implantation CTs directly, without the need for a pre-implantation CT of either ear, despite the significant artifacts introduced by the CI electrodes in those images. This new approach capitalizes on the physical relationship between the cochlear anatomy and the labyrinth, i.e., the rest of the inner ear.

In one aspect, the present invention is directed to a method for automatic segmentation of intra-cochlear anatomy in post-implantation CT image of bilateral cochlear implant recipients. In one embodiment, the method includes coarsely segmenting a labyrinth with a labyrinth surface chosen from a library of inner ear anatomy shapes, wherein the labyrinth surface is chosen such that its far points best approximate the far points portion of the labyrinth in the post-implantation CT image; creating a target specific active shape model (ASM) for each of the labyrinth and the structures-of-interest (SOIs) using a set of inner ear anatomy surfaces selected from the library of inner ear anatomy shapes such that the set of inner ear anatomy surfaces has the smallest dissimilarity quantity with the coarsely localized labyrinth surface in the post-implantation CT image; refining the coarsely segmented labyrinth surface by performing an ASM-based segmentation of the labyrinth using the target-specific ASM of the labyrinth to obtain a segmented labyrinth; and fitting the points of the target-specific ASM of the SOIs to their corresponding points on the segmented labyrinth to segment the SOIs in the post-implantation CT image.

In one embodiment, the method further comprises, prior to fitting the points of the target-specific ASM of the SOIs to their corresponding points on the segmented labyrinth, establishing offline a one-to-one point correspondence between the ASM points of the SOIs and the ASM points of the labyrinth.

In one embodiment, the coarsely segmenting step comprises determining the far points of the labyrinth in the target image by performing the ASM-based segmentation and fitting the far points of the labyrinth ASM; registering each labyrinth surface in the shape library to the target image using the transformation that minimizes the RMS distance between the far points on the library surface and the far points localized in the target image; and computing the dissimilarity quantity for each registered surface as the residual RMS, wherein the registered surface with the smallest dissimilarity quantity is used as the coarse segmentation.

In one embodiment, the ASM of a structure is created by providing a reference surface and a set of floating surfaces of the structure with a one-to-one point correspondence between the points on the reference surface and the points on each floating surface; registering each floating surface to the reference surface; building a target specific ASM using the registered surfaces by an eigenanalysis method, wherein the target specific ASM is represented by a mean shape of the structure; and storing the target specific ASM in the reference image, wherein the set of floating surfaces comprises a set of training surfaces, or the set of inner ear anatomy surfaces selected from the library of inner ear anatomy shapes.

In one embodiment, the step of registering each floating surface to the reference surface is performed with a seven degrees-of-freedom (7-DOF) transformation that minimizes a root-mean-squared (RMS) distance between the training surface and the reference surface.

In one embodiment, the reference surface and the set of floating surfaces of the structure are provided, using a reference image and a set of floating images containing the structure, by segmenting the structure in the reference image to create the reference surface of the structure; registering each floating image to the reference image to determine a corresponding registration transformation function for registering the floating image to the reference image; segmenting the structure in each floating image by projecting the reference surface of the reference image to the floating image with the corresponding registration transformation function to generate a floating surfaces of the structure in each floating image; and adjusting the generated floating surface of each floating image to create the set of floating surfaces of the structure.

In one embodiment, the step of registering each floating image to the reference image comprises downsampling the floating image and the reference image by a predetermined factor in each dimension; affinely registering the floating image to the reference image; cropping an ear region from the affinely registered floating image; affinely registering the ear region of the floating image to an ear region of the reference image at full image resolution; and non-rigidly registering the ear region of the floating image to the ear region of the reference image to obtain the registration transformation function. In one embodiment, the predetermined factor is a factor of 1-40 in each dimension.

In one embodiment, the ASM-based segmentation of the structure in a target image is performed by (a) projecting the mean shape of the ASM of the structure from the reference image to the target image using the registration transformation that registers the two images to determine an initial shape of the structure in the target image; (b) adjusting the initial shape of the structure by iteratively finding a candidate position for each point in the initial shape and fitting the ASM to these candidate positions in a weighted least squares sense to obtain an adjusted shape of the structure; and (c) iterating step (b) until the RMS distance between the adjusted shape and the initial shape at that iteration is smaller than a predetermined value.

In one embodiment, the library of inner ear anatomy surfaces is created from a plurality of pre-implantation CT images acquired from a number of subjects, by the ASM-based segmentation of the structure in each of the plurality of pre-implantation CT images.

In one embodiment, each shape in the library of inner ear anatomy shapes represents the labyrinth and the SOIs of an ear.

In one embodiment, the SOIs comprise scala tympani (ST), scala vestibuli (SV), spiral ganglion (SG), or a combination thereof.

In one embodiment, the labyrinth is a structure that externally bounds the intra-cochlear anatomy and includes the semicircular canals and the vestibule (SCCV).

In one embodiment, the far points of the labyrinth in the post-implantation CT image are far from implanted electrodes, thereby being unlikely to be affected by implant-related artifacts in the post-implantation CT image.

In another aspect, the invention relates to an automatic segmentation of inner ear anatomy of a living subject in a post-implantation CT image. In one embodiment, the method includes segmenting a region of the inner ear anatomy that is least likely to be affected by image artifacts in the post-implantation CT image so as to obtain a shape of the segmented region; selecting a set of inner ear anatomy shapes from a library of inner ear anatomy shapes, wherein each selected inner ear anatomy shape has the smallest dissimilarity quantity with the shape of the segmented region in the post-implantation CT image, and wherein each shape in the library of inner ear anatomy shapes represents a labyrinth and structures-of-interest (SOIs) of an ear; creating a target specific active shape model (ASM) for each of the labyrinth and the SOIs using the selected set of inner ear anatomy shapes; performing ASM-based segmentation of the labyrinth using the target-specific ASM of the labyrinth; and fitting the points of the target-specific ASM of the SOIs to their corresponding points on the segmented labyrinth to segment the SOIs in the post-implantation CT image.

In one embodiment, the method also includes, prior to fitting the points of the target-specific ASM of the SOIs to their corresponding points on the segmented labyrinth, establishing offline a one-to-one point correspondence between the ASM points of the SOIs and the ASM points of the labyrinth.

In one embodiment, the ASM of a structure is created by providing a reference surface and a set of floating surfaces of the structure with a one-to-one point correspondence between the points on the reference surface and the points on each floating surface; registering each floating surface to the reference surface; building a target specific ASM using the registered surfaces by an eigenanalysis method, wherein the target specific ASM is represented by a mean shape of the structure; and storing the target specific ASM in the reference image, wherein the set of floating surfaces comprises a set of training surfaces, or the set of inner ear anatomy surfaces selected from the library of inner ear anatomy shapes.

In one embodiment, the step of registering each floating surface to the reference surface is performed with a seven degrees-of-freedom (7-DOF) transformation that minimizes a root-mean-squared (RMS) distance between the training surface and the reference surface.

In one embodiment, the reference surface and the set of floating surfaces of the structure are provided, using a reference image and a set of floating images containing the structure, by segmenting the structure in the reference image to create the reference surface of the structure; registering each floating image to the reference image to determine a corresponding registration transformation function for registering the floating image to the reference image; segmenting the structure in each floating image by projecting the reference surface of the reference image to the floating image with the corresponding registration transformation function to generate a floating surfaces of the structure in each floating image; and adjusting the generated floating surface of each floating image to create the set of floating surfaces of the structure.

In one embodiment, the step of registering each floating image to the reference image comprises downsampling the floating image and the reference image by a predetermined factor in each dimension; affinely registering the floating image to the reference image; cropping an ear region from the affinely registered floating image; affinely registering the ear region of the floating image to an ear region of the reference image at full image resolution; and non-rigidly registering the ear region of the floating image to the ear region of the reference image to obtain the registration transformation function.

In one embodiment, the predetermined factor is a factor of 1-40 in each dimension.

In one embodiment, the ASM-based segmentation of the structure in a target image is performed by (a) projecting the mean shape of the ASM of the structure from the reference image to the target image using the registration transformation that registers the two images to determine an initial shape of the structure in the target image; (b) adjusting the initial shape of the structure by iteratively finding a candidate position for each point in the initial shape and fitting the ASM to these candidate positions in a weighted least squares sense to obtain an adjusted shape of the structure; and (c) iterating step (b) until the RMS distance between the adjusted shape and the initial shape at that iteration is smaller than a predetermined value.

In one embodiment, the library of inner ear anatomy surfaces is created from a plurality of pre-implantation CT images acquired from a number of subjects, by the ASM-based segmentation of the structure in each of the plurality of pre-implantation CT images.

In one embodiment, the step of fitting the target specific ASM of the SOIs to the segmented labyrinth to segmenting the SOIs comprises determining the mean shape of the SOIs' ASM as an initial SOI shape; determining a candidate point for each of the subset of SOI points that represent the external wall of the cochlea in the initial SOI shape as a corresponding point on the segmented labyrinth; assigning a first reliability weight for the candidate points and a second reliability weight for the remaining points; and fitting the SOIs' ASM to the candidate points in a weighted least squares sense. In one embodiment, the first reliability weight is about 0.99, while the second reliability weight is about 0.001.

In one embodiment, the SOIs comprise scala tympani (ST), scala vestibuli (SV), spiral ganglion (SG), or a combination thereof.

In one embodiment, the labyrinth is a structure that externally bounds the intra-cochlear anatomy and includes the semicircular canals and the vestibule (SCCV).

In one embodiment, the step of selecting the set of inner ear anatomy shapes from the library of inner ear anatomy shapes comprises mapping the labyrinth and SOI surfaces of each library subject onto the post-implantation CT image using a transformation that minimizes the root mean squared (RMS) distance between the library subject's SCCV points and the segmented target SCCV points; computing a dissimilarity quantity for each mapped library subject, wherein the dissimilarity quantity is defined to be the residual RMS of the registered library SCCV points; and selecting the set of inner ear anatomy shapes for which their dissimilarity quantity to the post-implantation CT image is the smallest.

In yet another aspect, the invention relates to a method for automatic segmentation of inner ear anatomy of a living subject in a post-implantation CT image. In one embodiment, the method comprises segmenting a region of the inner ear anatomy as a landmark structure in the post-implantation CT image so as to obtain a shape of the segmented landmark structure; and segmenting inner ear structures of interest (SOIs) in the post-implantation CT image using the segmented landmark structure.

In one embodiment, the region of the inner ear anatomy is in close proximity to the SOIs and is not entirely affected by image artifacts.

In one embodiment, the region of the inner ear anatomy is a lateral part of the labyrinth that is a structure externally bounding the intra-cochlear anatomy and includes the semicircular canals and the vestibule (SCCV).

In one embodiment, the step of segmenting the landmark structure comprises mapping a shape of the landmark chosen from a library of inner ear anatomy shapes to the post-implantation CT image, wherein each shape in the library of inner ear anatomy shapes represents the landmark structure and the SOIs of an ear.

In one embodiment, the step of segmenting the SOIs comprises selecting a set of inner ear anatomy shapes from the library of inner ear anatomy shapes in accordance with the shape of the segmented landmark structure, wherein each selected inner ear anatomy shape has the smallest dissimilarity quantity with the shape of the segmented landmark structure in the post-implantation CT image; creating a target specific active shape model (ASM) for each of the landmark structure and the SOIs using the selected set of inner ear anatomy shapes; performing ASM-based segmentation of the landmark structure using the target-specific ASM of the landmark structure; and fitting the points of the target-specific ASM of the SOIs to their corresponding points on the segmented landmark structure to segment the SOIs in the post-implantation CT image.

In one embodiment, the method further comprises, prior to fitting the points of the target-specific ASM of the SOIs to their corresponding points on the segmented landmark structure, establishing offline a one-to-one point correspondence between the ASM points of the SOIs and the ASM points of the landmark structure.

In one embodiment, the ASM-based segmentation of the structure in a target image is performed by (a) projecting the mean shape of the ASM of the structure from the reference image to the target image using the registration transformation that registers the two images to determine an initial shape of the structure in the target image; (b) adjusting the initial shape of the structure by iteratively finding a candidate position for each point in the initial shape and fitting the ASM to these candidate positions in a weighted least squares sense to obtain an adjusted shape of the structure; and (c) iterating step (b) until the RMS distance between the adjusted shape and the initial shape at that iteration is smaller than a predetermined value.

In one embodiment, the library of inner ear anatomy surfaces is created from a plurality of pre-implantation CT images acquired from a number of subjects, by the ASM-based segmentation of the structure in each of the plurality of pre-implantation CT images.

In a further aspect, the present invention also relates to a non-transitory computer-readable medium storing instructions which, when executed by one or more processors, cause a computer or system to perform the method for automatic segmentation of inner ear anatomy of a living subject in a post-implantation CT image, as disclosed above.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. The same reference numbers may be used throughout the drawings to refer to the same or like elements in the embodiments.

FIGS. 1A and 1B show surfaces of the ST (red), the SV (blue), and the SG (green). FIG. 1B also shows a surface model of a CI electrode array inserted into the ST is shown. FIG. 1C shows surfaces of the AR (green), the ST (transparent red) and the SV (transparent blue).

DETAILED DESCRIPTION OF THE INVENTION

Figure 1E:
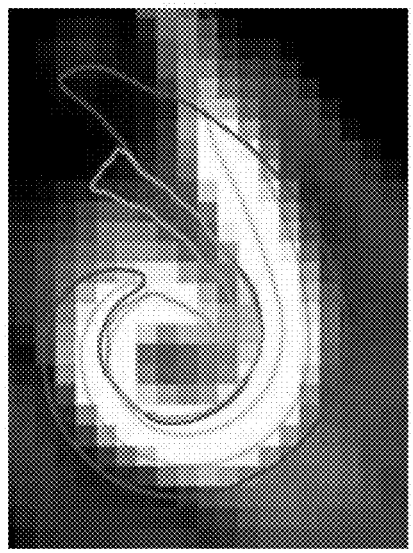
FIGS. 1D and 1E show contours of the ST (red), the SG (green), and the electrodes (purple) in the coronal view of a pre-implantation CT and a corresponding post-implantation CT.
Figure 1G:
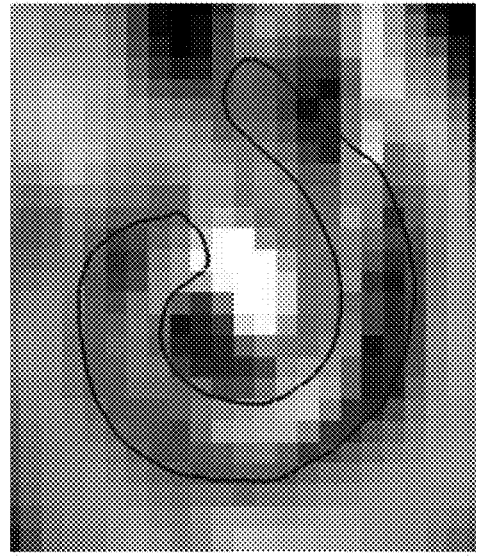
FIGS. 1F and 1G show are contours of the SV (blue) in the coronal view of a pre-implantation CT and a corresponding post-implantation CT.
Figure 1D:
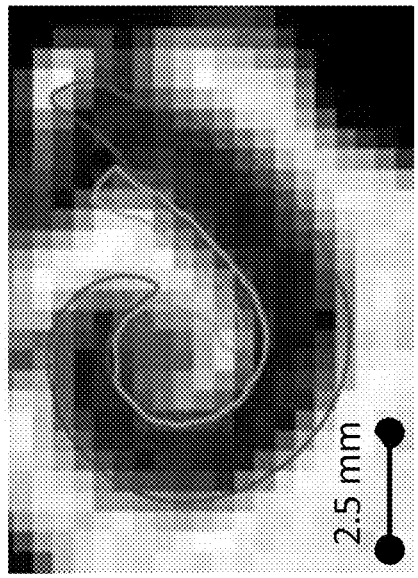
Figure 1F:
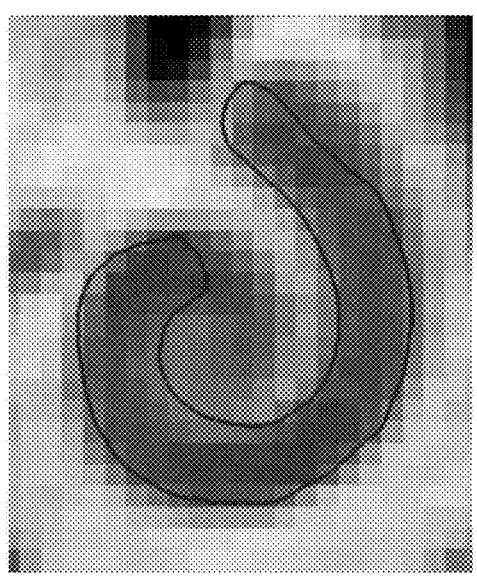

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the FIGS. is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this invention, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

The description below is made as to the embodiments of the invention in conjunction with the accompanying drawings. In accordance with the purposes of this invention, as embodied and broadly described herein, this invention, in one aspect, relates to methods (algorithms) for automatic segmentation of the internal structures of the ear in post-implantation CT images directly without requiring a pre-implantation CT image of either ear for bilateral cochlear implant recipients.

Existing segmentation methods cannot be used for segmenting the inner ear anatomy in a post-implantation CT image directly without using a pre-implantation CT image of one of the ears. This is because the cochlear anatomy is obscured by image artifacts caused by the implanted electrodes in the post-implantation CT image. According to algorithms of this invention, segmentation of the inner ear anatomy can be achieved in a post-implantation CT image directly without requiring a pre-implantation CT image of either ear. The invented algorithms can be used to extend the CI programming technique to the subpopulation of bilateral CI recipients for whom a CT image has not been acquired prior to implantation.

Generally, the algorithms include, among other things, precise localizations of the scala tympani (ST), the scala vestibuli (SV), the spiral ganglion (SG), and the labyrinth that includes the external wall of the cochlea, the semicircular canals and the vestibule (SCCV), by mapping respective surfaces that are selected from a library of inner ear anatomy shapes, construction and use of shape models that are specific to the post-implantation CT image for refining the mapped library surfaces, creation of the library of inner ear anatomy shapes, and construction of a statistical shape model for the labyrinth.

In certain embodiments, the algorithms are to first identify the SCCV regions in the post-implantation CT images, and then use this portion of the labyrinth, which serves as a landmark structure, to map inner ear structure surfaces chosen from a library of inner ear anatomy surfaces. The inner ear structure surfaces are chosen based on how well their shape of the SCCV regions matches the shape of the corresponding structures identified in the post-implantation CT. Then, active shape models for the structures are created using the subset of surfaces chosen from the library of inner ear anatomy surfaces based on their similarity to the SCCV shapes identified in the post-implantation CT. Finally, the initial segmentations, which are obtained by mapping library surfaces, are refined using an active shape-model (ASM)-based segmentation method.

Figure 2:
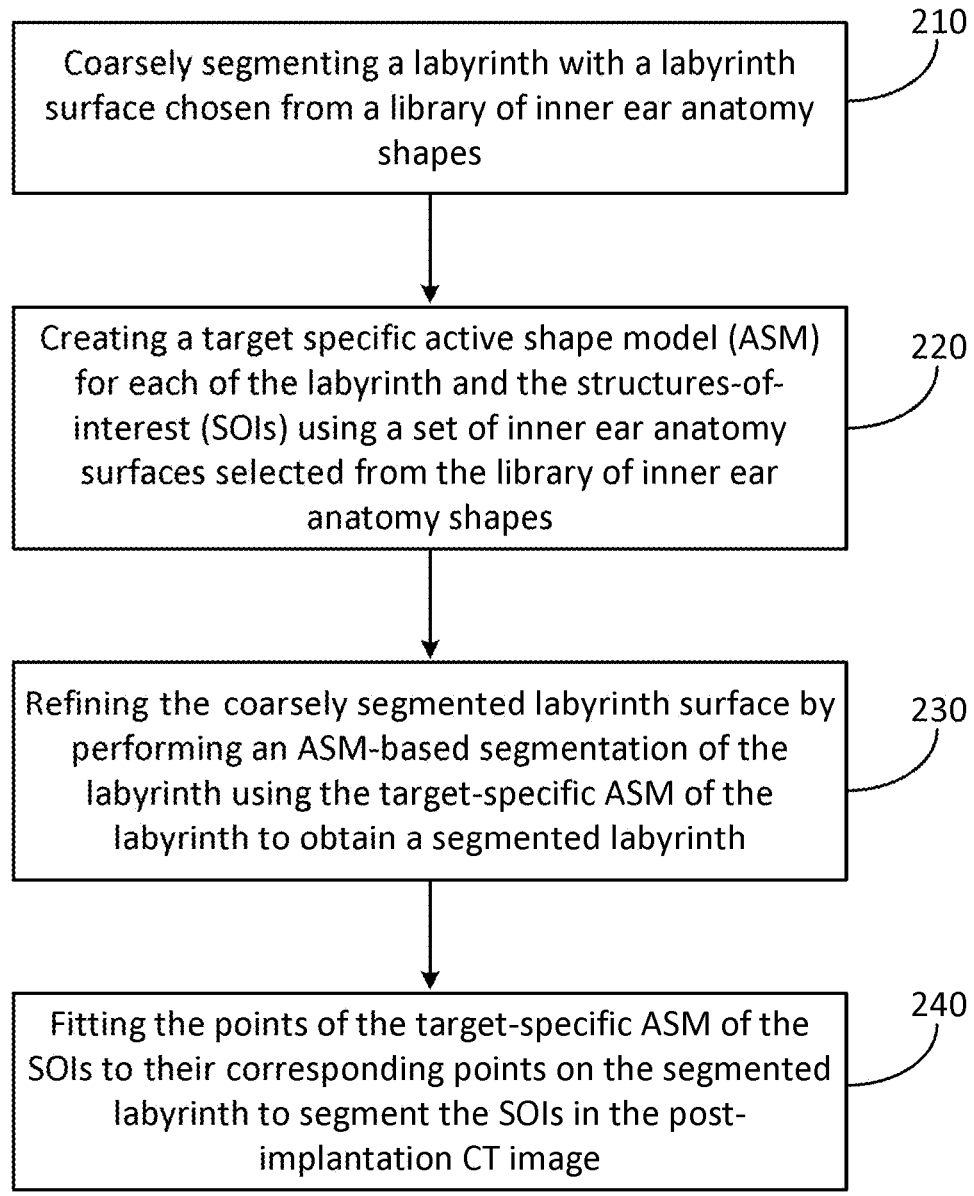
FIG. 2 shows a flowchart of automatic segmentation of inner ear anatomy of a living subject in a post-implantation CT image according to one embodiment of the invention.

In one aspect, the present invention is directed to a method for automatic segmentation of intra-cochlear anatomy in post-implantation CT image of bilateral cochlear implant recipients. As shown in FIG. 2, the method includes the following steps: at step 210, a labyrinth in the post-implantation CT image is coarsely segmented with a labyrinth surface chosen from a library of inner ear anatomy shapes, where the labyrinth surface is chosen such that its far points best approximate the far points portion of the labyrinth in the post-implantation CT image. The labyrinth is a structure that externally bounds the intra-cochlear anatomy and includes the SCCV. As discussed below, the labyrinth is used as a landmark structure. The far points of the labyrinth in the post-implantation CT image are far from implanted electrodes, thereby being unlikely to be affected by implant-related artifacts in the post-implantation CT image.

In one embodiment, the coarsely segmenting step comprises determining the far points of the labyrinth in the target image by performing the ASM-based segmentation and fitting the far points of the labyrinth ASM; registering each labyrinth surface in the shape library to the target image using the transformation that minimizes the RMS distance between the far points on the library surface and the far points localized in the target image; and computing the dissimilarity quantity for each registered surface as the residual RMS, wherein the registered surface with the smallest dissimilarity quantity is used as the coarse segmentation.

At step 220, a target specific active shape model (ASM) for each of the labyrinth and the structures-of-interest (SOIs) is created using a set of inner ear anatomy surfaces selected from the library of inner ear anatomy shapes such that the set of inner ear anatomy surfaces has the smallest dissimilarity quantity with the coarsely localized labyrinth surface in the post-implantation CT image. The SOIs include ST, SV, SG, or a combination thereof. Each shape in the library of inner ear anatomy shapes represents the labyrinth and the SOIs of an ear At step 230, the coarsely segmented labyrinth surface is refined by performing an ASM-based segmentation of the labyrinth using the target-specific ASM of the labyrinth to obtain a segmented labyrinth.

At step 240, the points of the target-specific ASM of the SOIs are fitted to their corresponding points on the segmented labyrinth to segment the SOIs in the post-implantation CT image.

Further, prior to fitting the points of the target-specific ASM of the SOIs to their corresponding points on the segmented labyrinth, the method may comprise establishing offline a one-to-one point correspondence between the ASM points of the SOIs and the ASM points of the labyrinth.

Figure 3:
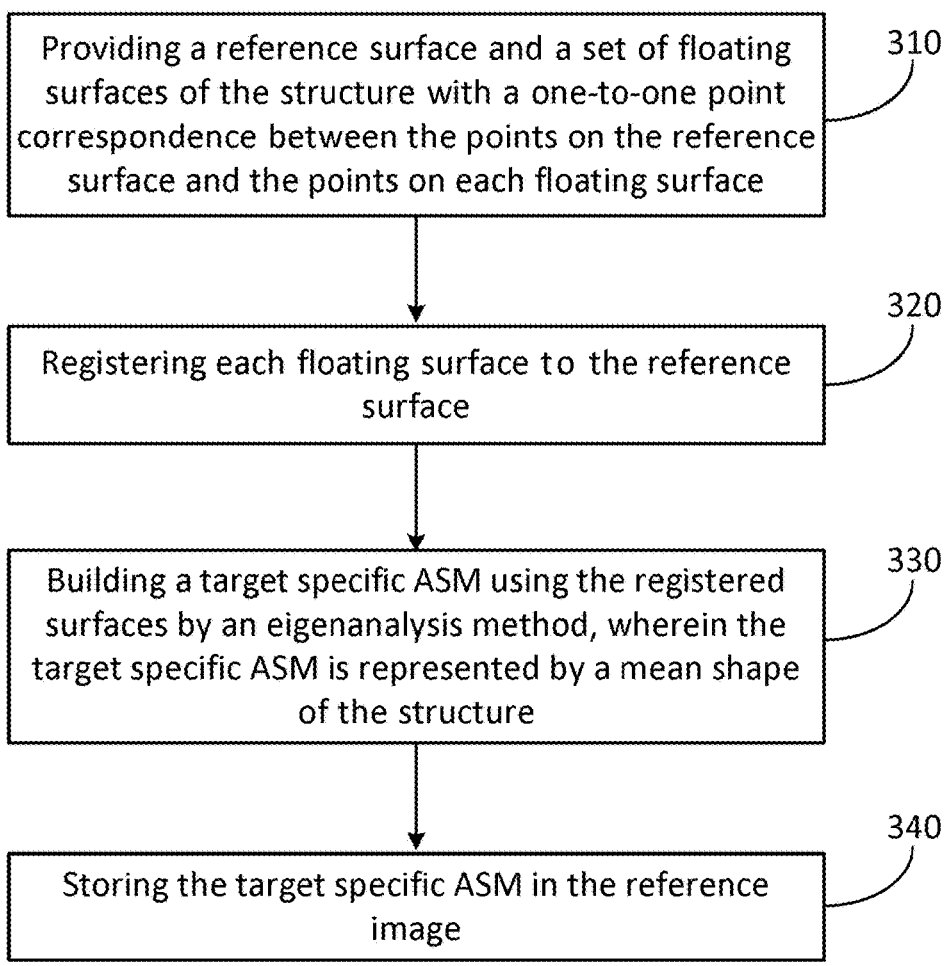
FIG. 3 shows a flowchart of creating an ASM of a structure according to one embodiment of the invention.

Referring to FIG. 3, a flow chart of creating ASM of a structure is shown according to one embodiment of the invention. The ASM of the structure is created by providing a reference surface and a set of floating surfaces of the structure with a one-to-one point correspondence between the points on the reference surface and the points on each floating surface (at step 310); registering each floating surface to the reference surface (at step 320); building a target specific ASM using the registered surfaces by an eigenanalysis method (at step 330), where the target specific ASM is represented by a mean shape of the structure; and storing the target specific ASM in the reference image (at step 310). The set of floating surfaces comprises a set of training surfaces, or the set of inner ear anatomy surfaces selected from the library of inner ear anatomy shapes.

In one embodiment, the step 320 of registering each floating surface to the reference surface is performed with a seven degrees-of-freedom (7-DOF) transformation that minimizes a root-mean-squared (RMS) distance between the training surface and the reference surface.

In one embodiment, the reference surface and the set of floating surfaces of the structure are provided, using a reference image and a set of floating images containing the structure, by segmenting the structure in the reference image to create the reference surface of the structure; registering each floating image to the reference image to determine a corresponding registration transformation function for registering the floating image to the reference image; segmenting the structure in each floating image by projecting the reference surface of the reference image to the floating image with the corresponding registration transformation function to generate a floating surfaces of the structure in each floating image; and adjusting the generated floating surface of each floating image to create the set of floating surfaces of the structure.

Figure 5:
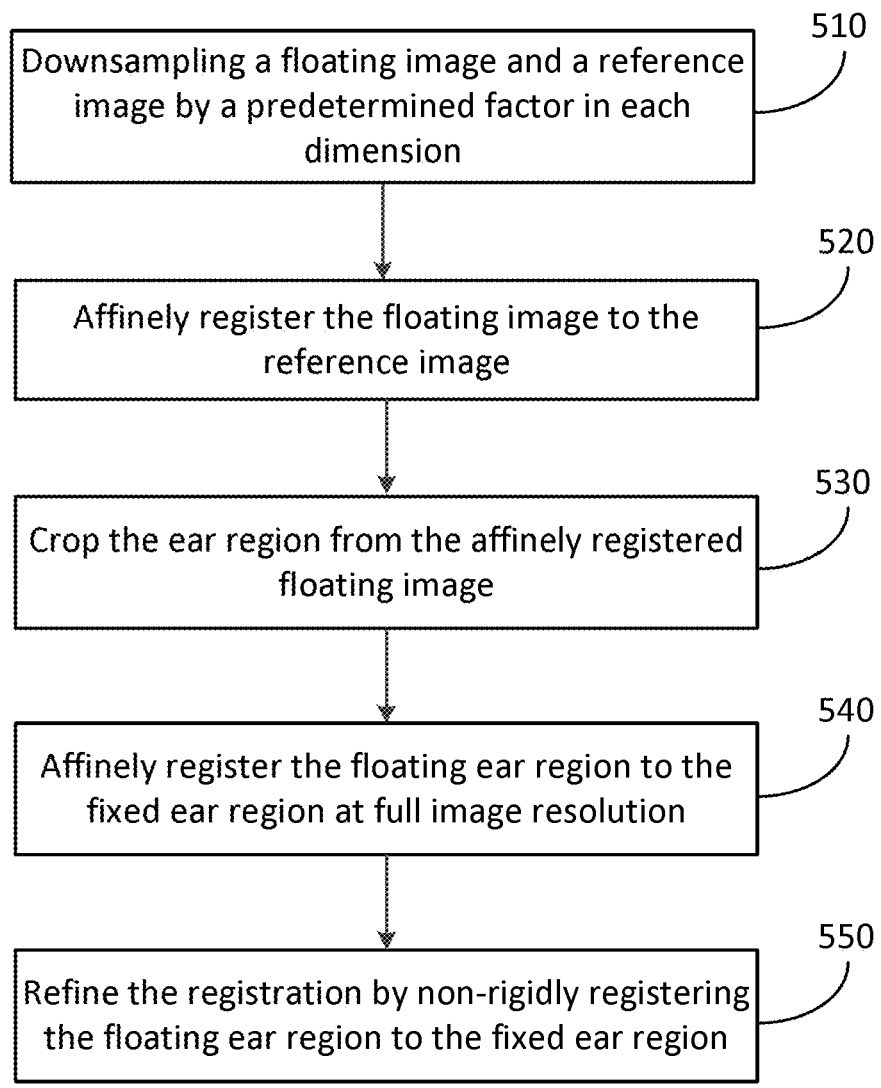
FIG. 5 shows a flowchart of an image registration process according to one embodiment of the invention.

FIG. 5 shows a flow chart of registering a floating (target/training) image to a reference image according to one embodiment of the invention. This image registration process is also used to obtain a registration transformation function. In this embodiment, the floating image and the reference image are downsampled by a predetermined factor in each dimension at step 510. In one embodiment, the predetermined factor is a factor of 1-40 in each dimension, for example, the predetermined factor is a factor of 4. At step 520, the floating image is affinely registered to the reference image. At step 530, an ear region is cropped from the affinely registered floating image. At step 530, the ear region of the floating image is affinely registered to an ear region of the reference image at full image resolution. At step 550, the ear region of the floating image is non-rigidly registered to the ear region of the reference image to obtain the registration transformation function.

Figure 4:
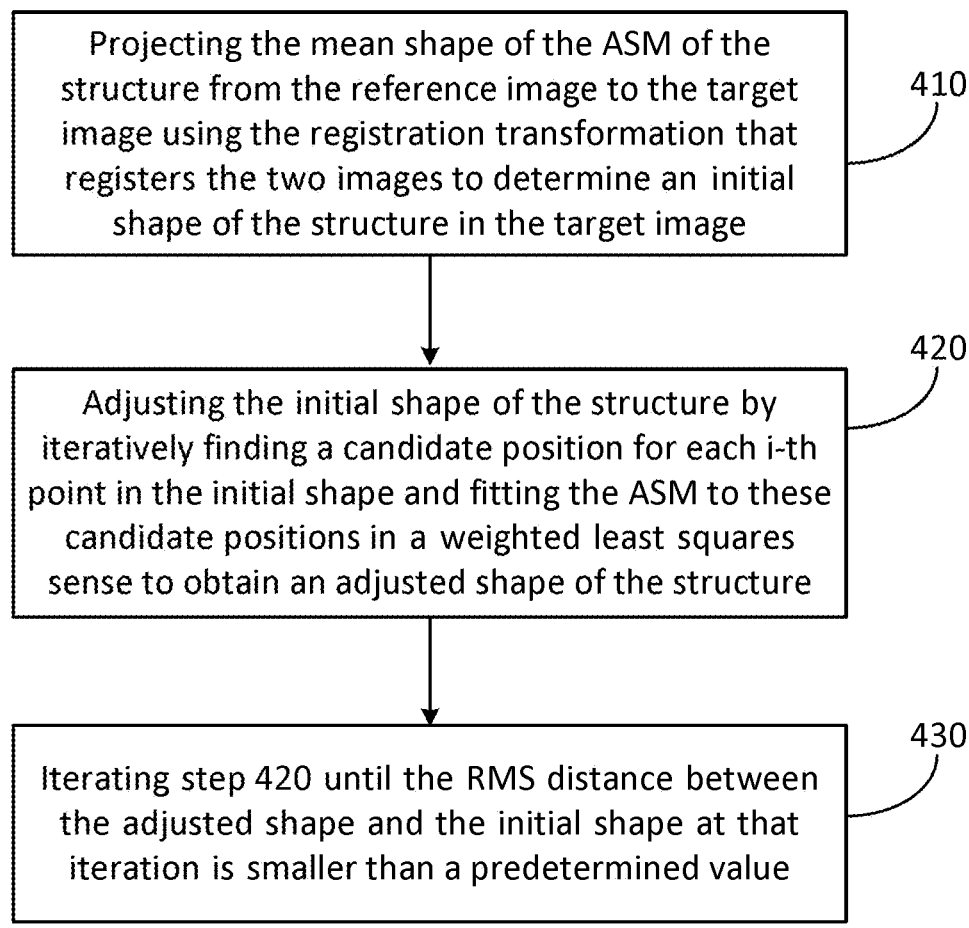
FIG. 4 shows a flowchart of an ASM-based segmentation of a structure according to one embodiment of the invention.

Referring to FIG. 4, the process of the ASM-based segmentation of the structure in a target image is shown according to one embodiment of the invention. Specifically, at step 410, the mean shape of the ASM of the structure from the reference image is projected to the target image using the registration transformation that registers the two images to determine an initial shape of the structure in the target image. At step 420, the initial shape of the structure is adjusted by iteratively finding a candidate position for each point in the initial shape and fitting the ASM to these candidate positions in a weighted least squares sense to obtain an adjusted shape of the structure. And at step 430, iterating step 420 until the RMS distance between the adjusted shape and the initial shape at that iteration is smaller than a predetermined value.

Figure 6:
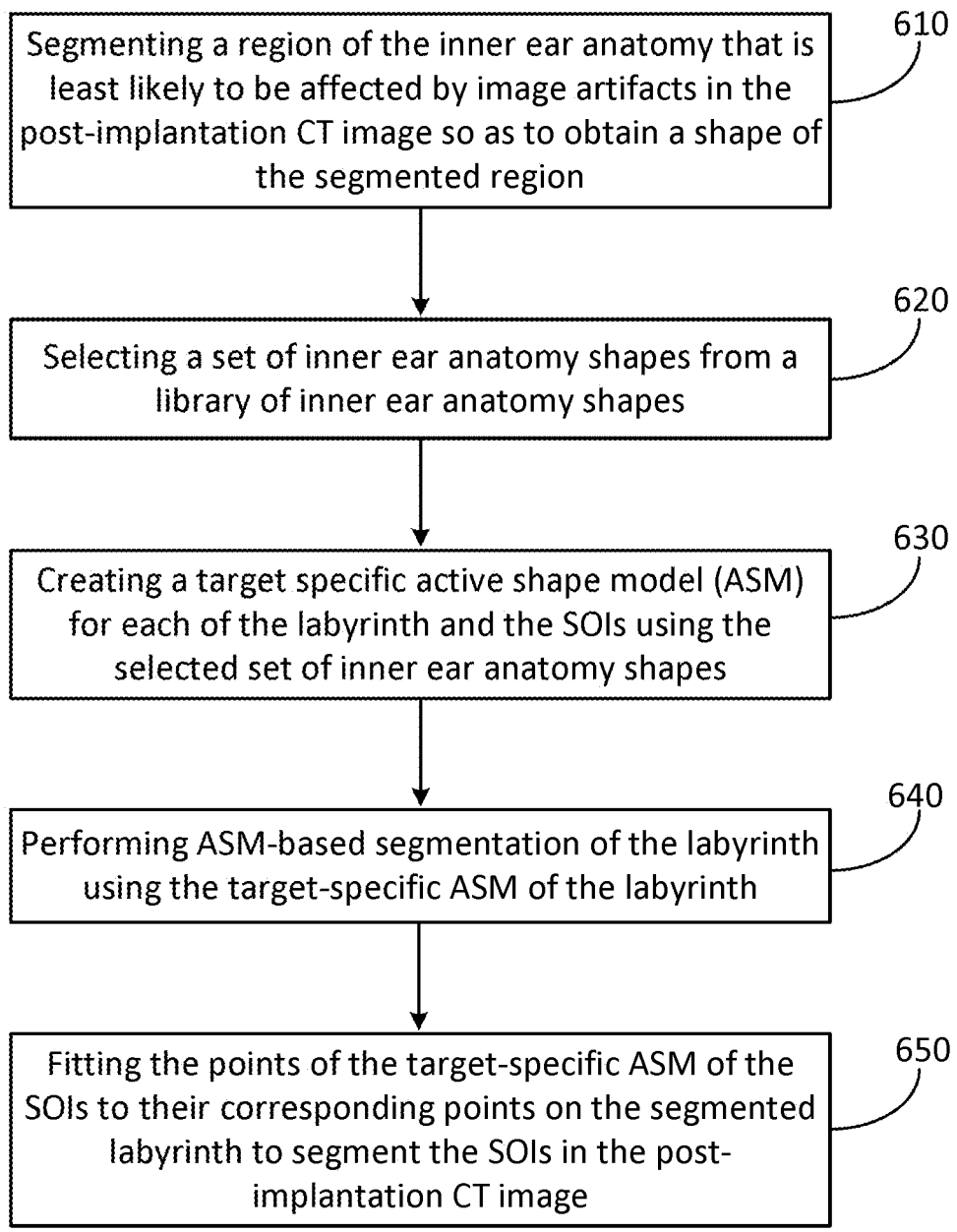
FIG. 6 shows a flowchart of automatic segmentation of inner ear anatomy of a living subject in a post-implantation CT image according to one embodiment of the invention.

Referring to FIG. 6, the algorithm/method for an automatic segmentation of inner ear anatomy of a living subject in a post-implantation CT image is shown according to one embodiment of the invention. In exemplary embodiment, the method includes the following steps: At step 610, a region of the inner ear anatomy that is least likely to be affected by image artifacts in the post-implantation CT image is segmented so as to obtain a shape of the segmented region. In one embodiment, the region is the labyrinth that is a structure that externally bounds the intra-cochlear anatomy and includes the SCCV. The SOIs includes ST, SV, SG, or a combination thereof.

At step 620, a set of inner ear anatomy shapes is selected from a library of inner ear anatomy shapes, where each selected inner ear anatomy shape has the smallest dissimilarity quantity with the shape of the segmented region in the post-implantation CT image, and each shape in the library of inner ear anatomy shapes represents a labyrinth and structures-of-interest (SOIs) of an ear.

In one embodiment, step 620 of selecting the set of inner ear anatomy shapes from the library of inner ear anatomy shapes comprises mapping the labyrinth and SOI surfaces of each library subject onto the post-implantation CT image using a transformation that minimizes the root mean squared (RMS) distance between the library subject's SCCV points and the segmented target SCCV points; computing a dissimilarity quantity for each mapped library subject, wherein the dissimilarity quantity is defined to be the residual RMS of the registered library SCCV points; and selecting the set of inner ear anatomy shapes for which their dissimilarity quantity to the post-implantation CT image is the smallest.

At step 630, a target specific active shape model (ASM) for each of the labyrinth and the SOIs is created using the selected set of inner ear anatomy shapes.

At step 640, ASM-based segmentation of the labyrinth is performed using the target-specific ASM of the labyrinth.

At step 640, the points of the target-specific ASM of the SOIs is fitted to their corresponding points on the segmented labyrinth to segment the SOIs in the post-implantation CT image.

In one embodiment, step 640 of fitting the target specific ASM of the SOIs to the segmented labyrinth to segment the SOIs comprises the steps of determining the mean shape of the SOIs' ASM as an initial SOI shape; determining a candidate point for each of the subset of SOI points that represent the external wall of the cochlea in the initial SOI shape as a corresponding point on the segmented labyrinth; assigning a first reliability weight for the candidate points and a second reliability weight for the remaining points; and fitting the SOIs' ASM to the candidate points in a weighted least squares sense. In one embodiment, the first reliability weight is about 0.99, while the second reliability weight is about 0.001.

In addition, prior to fitting the points of the target-specific ASM of the SOIs to their corresponding points on the segmented labyrinth, the method also includes establishing offline a one-to-one point correspondence between the ASM points of the SOIs and the ASM points of the labyrinth.

In yet another aspect of the invention, a method for automatic segmentation of inner ear anatomy of a living subject in a post-implantation CT image comprises segmenting a region of the inner ear anatomy as a landmark structure in the post-implantation CT image so as to obtain a shape of the segmented landmark structure; and segmenting inner ear SOIs in the post-implantation CT image using the segmented landmark structure.

In one embodiment, the region of the inner ear anatomy is in close proximity to the SOIs and is not entirely affected by image artifacts. The region of the inner ear anatomy is a lateral part of the labyrinth that is a structure externally bounding the intra-cochlear anatomy and includes the SCCV.

In one embodiment, the step of segmenting the landmark structure comprises mapping a shape of the landmark chosen from a library of inner ear anatomy shapes to the post-implantation CT image, wherein each shape in the library of inner ear anatomy shapes represents the landmark structure and the SOIs of an ear.

In one embodiment, the step of segmenting the SOIs comprises selecting a set of inner ear anatomy shapes from the library of inner ear anatomy shapes in accordance with the shape of the segmented landmark structure, wherein each selected inner ear anatomy shape has the smallest dissimilarity quantity with the shape of the segmented landmark structure in the post-implantation CT image; creating a target specific ASM for each of the landmark structure and the SOIs using the selected set of inner ear anatomy shapes; performing ASM-based segmentation of the landmark structure using the target-specific ASM of the landmark structure; and fitting the points of the target-specific ASM of the SOIs to their corresponding points on the segmented landmark structure to segment the SOIs in the post-implantation CT image.

It should be noted that all or a part of the steps according to the embodiments of the present invention is implemented by hardware or a program instructing relevant hardware. Yet another aspect of the invention provides a non-transitory computer readable storage medium/memory which stores computer executable instructions or program codes. The computer executable instructions or program codes enable a computer or a similar computing system to complete various operations in the above disclosed method for privilege management. The storage medium/memory may include, but is not limited to, high-speed random access medium/memory such as DRAM, SRAM, DDR RAM or other random access solid state memory devices, and non-volatile memory such as one or more magnetic disk storage devices, optical disk storage devices, flash memory devices, or other non-volatile solid state storage devices.

Without intent to limit the scope of the invention, examples and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

EXAMPLE I

In this example, the shape library-based method for automatic segmentation of inner ear anatomy in a post-implantation CT was applied to 10 ears, which achieves overall mean and maximum errors of 0.209 and 0.98 mm, respectively. The results suggest that the method is accurate enough for extending the IGCIP strategies based solely on post-implantation CTs.

Figure 7A:
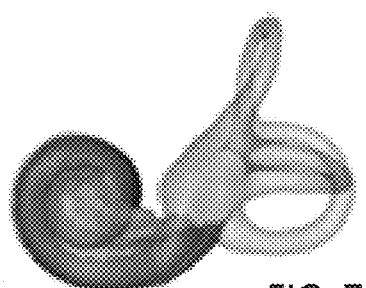
FIG. 7A shows surfaces of a labyrinth (transparent orange) and of the intra-cochlear anatomy (ST (transparent red), SV (transparent blue), and SG (transparent green)).
Figure 7B:
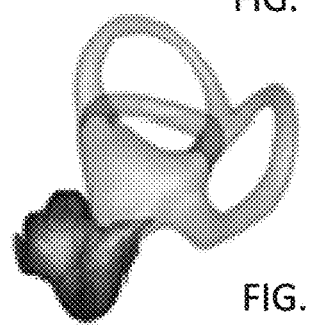
FIG. 7B shows the same structures in a different orientation.

According to this exemplary embodiment of the method of the invention, the entire labyrinth, which is used as a landmark structure, is localized by (1) coarsely estimating its position using a shape chosen from a library of labyrinth shapes, (2) automatically creating a statistical shape model that is specific to the subject, and (3) refining the coarse estimate by performing a statistical shape model-based segmentation. The labyrinth is a structure that shares the external wall of the cochlea with the intra-cochlear anatomy and that also includes the semi-circular canals. FIGS. 7A and 7B show a surface of the labyrinth and the intra-cochlear structures that it externally bounds. Next, the SOIs are segmented by fitting the subset of SOI model points, that represent the external wall of the cochlea (see FIGS. 7D and 7E), to the part of the labyrinth that represent the same (see FIG. 7C). To do the fitting, a one-to-one point correspondence between the subset of SOI model points and the subset of labyrinth model points that represent the exterior of the cochlea is established offline. The exterior region of the cochlea, which is used to fit the SOIs model, is the only portion of the SOIs that has contrast in CT and can also be localized by the labyrinth.

I.1. Data

In this example, several groups of head CT scans were used, which are presented in Table I. The scans were acquired from several conventional scanners and a low-dose flat-panel volumetric CT (fpVCT) scanner (Xoran Technologies xCAT® ENT). Conventional CTs of 70 subjects are used for creating SOI and labyrinth shapes library as discussed in Section I.4, conventional CTs of 25 subjects are used for creating an active shape model (ASM) of the labyrinth as discussed in Section I.4, fpVCT scans of 14 subjects are used for creating an intensity model for each point on an ASM of the labyrinth as discussed in Section I.5.2, and CT-fpVCT pairs of 8 subjects are used for validating the segmentation results as discussed in Section I.5.3. The validation dataset (dataset 5) is constructed such that it allows us to (1) generate automatic segmentations on post-implantation CTs using the invented algorithm, (2) register the post-implantation CTs to the corresponding pre-implantation CTs, and (3) validate the results by comparing registered automatic segmentations to ground truth segmentations established on the pre-implantation CTs. Typical voxel size for conventional CTs is $0.25 \times 0.25 \times 0.3$ mm$^3$; for flat-panel CTs it is $0.4 \times 0.4 \times 0.4$ mm$^3$.

Table I summarizes the characteristics of the various sets of CT scans used for evaluation the method (algorithm) according to certain embodiments of the present invention. Age of subjects included in this exemplary study ranged from 18 to 90 years. The CT scans were acquired from several conventional scanners (GE BrightSpeed, LightSpeed Ultra; Siemens Sensation 16; and Philips Mx8000 IDT, iCT 128, and Brilliance 64) and a low-dose flat-panel volumetric CT (fpVCT) scanner (Xoran Technologies xCAT® ENT). Conventional CT scans of 10 subjects were used for symmetry analysis as described in Section I.3. Conventional CT scans of 18 subjects were used for active shape model (ASM) creation as discussed in Section I.4. fpVCT scans of 14 subjects were used for intensity gradient model (IGM) creation as discussed in Section I.5.2. 18 CT-fpVCT pairs of scans were used for segmentation validation as discussed in Section I.5.3. Typical scan resolution for conventional CT scans is $768 \times 768 \times 145$ voxels with $0.2 \times 0.2 \times 0.3$ mm$^3$ voxel size, and for fpVCT scans is $700 \times 700 \times 360$ voxels and $0.3 \times 0.3 \times 0.3$ or $0.4 \times 0.4 \times 0.4$ mm$^3$.

TABLE 1

Datasets Used in Example I

| Data set | Purpose | Data set size | Acquisition Xoran fpVCT | Acquisition Conventional | Numbers of CIs No CIs | Numbers of CIs One CI | Numbers of CIs Two CIs |
|---|---|---|---|---|---|---|---|
| 1 | Reference (atlas) | 1 | | x | x | | |
| 2 | Shape library creation | 70 | | x | x | | |
| 3 | Labyrinth ASM creation | 25 | | x | x | | |
| 4 | Intensity model creation | 14 | x | | x | | |
| 5 | Segmentation Validation | 6 | | x | x | | |
| | | | x | | | x | |
| | | 2 | | x | x | | |
| | | | x | | | | x |

I.2. Image Registration Methods

In this subsection, we present the image-to-image registration process used at various steps throughout this study. Given a "fixed" image, i.e., an atlas or reference image, and a "floating" image, i.e., the target image, we use the process outlined in FIG. 5 to register them. First, at step 510, both the floating image and the fixed image are downsampled by a predetermined factor in a range of 1-40 in each dimension. At step 520, we affinely register the entire but downsampled images using an intensity-based affine registration method [9, 10]. For example, the floating image is affinely registered to the fixed image, after downsampling both images by the factor of 4 in each dimension.

In one embodiment, the predetermined factor is a factor of four. Then, the ear region is cropped from the affinely registered floating image at step 530. Next, we refine this registration by performing intensity-based affine registration at full image resolution on a pre-determined region that encompasses the ear structures at step 540. Finally, we further refine the registration by performing intensity-based non-rigid registration on the ear region [11], i.e., non-rigidly register the floating ear region to the fixed ear region, at step 550.

I.3. Active Shape Model (ASM)-Based Segmentation

Various processes described in the following subsections rely on the creation of an active shape model (ASM) and performing active shape segmentation. Thus, in the following subsections describes the general ASM framework.

I.3.1. Active Shape Model (ASM) Creation

Given a reference surface and a set of training surfaces of a structure with a one-to-one point correspondence between the points on the reference surface and the points on each training surface, the following steps are performed to create an ASM of a structure. First, each training surface is registered to the reference surface with a 7-DOF (three translations, three rotations, one isotropic scaling) transformation that minimizes the root-mean-squared (RMS) distance between the surfaces. Next, the registered surfaces are used to build the structure ASM according to the procedure described by Cootes in [12]. Finally, the ASM is stored in the reference image space. The ASM is represented by the mean shape $\{\bar{x}_l\}_{i=0}^{N-1}$, with N being the number of points in the shape, and L eigenvectors $U = [u_0, u_1, \ldots, u_{L-1}]$ that are corresponding to the largest eigenvalues $[\lambda_0, \lambda_1, \ldots, \lambda_{L-1}]$. Mathematically, $$\{\lambda_l, u_l\}_{l=0}^{L-1}: \lambda_l u_l = X u_l \qquad (I.1)$$

where X is the covariance matrix of the points on registered surfaces.

I.3.2. Active Shape Segmentation

Active shape segmentation of the structure is performed by fitting the ASM to an initial estimate of the shape. This process includes three main steps:

(1) Shape initialization: an initial coarse estimate of the shape $\{x_i\}_{i=0}^{N-1}$ is determined by projecting the mean shape $\{\bar{x}_l\}_{i=0}^{N-1}$ from the reference image space to the target image space using the registration transformation that registers the two images. This registration transformation is computed using the image-to-image registration process described in Section I.2.

(2) Shape adjustment: the initial shape is adjusted by iteratively finding a candidate position for each i-th point in the initial shape and fitting the active shape model to these candidate positions in a weighted least squares sense. The candidate position $x'_i$ for each initial point $x_i$ is determined along the surface normal $\hat{n}_i$ in the interval $[-1.5, 1.5]$ mm, equivalently $$x'_i = x_i + \Delta d \cdot k_{min} \cdot \hat{n}_i, \qquad (I.2)$$

where $\Delta d = 0.15$ mm, and $k_{min}$ is chosen as, $$k_{min} = \arg\min_k C_i(k): k \in \{-10, -9, \ldots, 10\}, \qquad (I.3)$$

i.e., the candidate position for the i-th point is the position at which the cost function $C_i(\cdot)$ is the smallest cost value in the interval [−1.5, 1.5] mm along the surface normal $\hat{n}_i$. The cost function is tailored to the type of image as described in the following section. Then, the active shape model is fitted to the candidate points $\{x'_i\}_{i=0}^{N-1}$ to obtain an adjusted shape $\{x''_i\}_{i=0}^{N-1}$, given by $$x''_i = \varphi^{-1}(\bar{x}_i + \Sigma_{l=0}^{L-1} b_l u_{l,i}) \tag{I.4}$$

where b, a vector of parameters that defines the shape, is given by $$b = [b_0, b_1, \ldots, b_{L-1}] = (U^T W^T W U)^{-1} U^T W^T W d, \tag{I.5}$$

and $= \{d_i\}_{i=0}^{N-1}$, defined as, $$d_i = \varphi(x'_i) - \bar{x}_i \text{ for } i \in \{0, N-1\}, \tag{I.6}$$

is the residual between the mean shape and candidate points, after they are registered to the mean shape with a 7-DOF (three translation, three rotation, and one isotropic scaling) transformation $\varphi$, computed as $$\varphi = \arg \min_{\varphi} \Sigma_{l=0}^{L-1} w_i^2 \|\varphi(x'_i) - \bar{x}_i\|^2. \tag{I.7}$$

A reliability weight $w_i \in [0, 1]$ is assigned for each candidate point. The reliability weight computation, as explained in the following sections, is tailored for the type of image to b e segmented. The weight matrix $W = \text{diag}([w_0, w_1, \ldots, w_{N-1}])$, with $w_i = [w_i, w_i, w_i]$, in Eqn. (I.5) is designed so that candidate points with high reliability have more influence on the least squares model fitting.

(3) Iterative shape adjustment: the shape adjustment process is iterated until the RMS distance between the adjusted shape and the initial shape at that iteration is small, specifically until $$\left( \frac{1}{N} \sum_{i=0}^{N-1} \|x''_i - x_i\|^2 \right)^{1/2} < \varepsilon$$

is satisfied, where $\varepsilon$ is empirically set to 0.01 mm.

In summary, given an ASM of a structure and its initial shape estimate, the ASM iteratively fitted to segment the structure. At each iteration, a candidate position for each i-th point is determined using Eqn. (I.2); a weight for each i-th candidate point is re-computed; and finally an adjusted shape is determined by fitting the ASM to the candidate points in a weighted least squares sense using Eqn. (I.4).

I.4. Shape Library Creation

The segmentation approach, as discussed in the next subsection, relies on first determining a coarse estimate of the labyrinth, which is used as a landmark, and of the intra-cochlear structures, which are the SOIs, by mapping surfaces of the labyrinth and SOIs chosen from a library of labyrinth and SOI surfaces to the subject's CT images. To enable this approach, a library of internal ear structures segmented in a number of subject's pre-implantation CTs is created. Specifically, the set of CTs in dataset 2 listed in Table I is used to create a library of surfaces that represent the labyrinth and SOIs of each subject's left or right ear, chosen randomly.

To produce a surface of the labyrinth in each CT in this dataset, an ASM-based segmentation of the labyrinth in the CT is performed using the active shape segmentation process described in Section I.3.2. The labyrinth ASM used in this step is created offline, using the reference CT in dataset 1 and the set of training CTs in dataset 3, according to the process previously reported in [8] for the same purpose.

When segmenting an image with this model, the cost function $C_i(k)$ used for candidate position selection in Eqn. (I.3) is given by $$C_i(k) = -|I(x_i + \Delta d \cdot (k+1) \cdot \hat{n}_i) - I(x_i + \Delta d \cdot (k-1) \cdot \hat{n}_i)|, \tag{I.8}$$

where $I(\cdot)$ is image intensity in the CT at a given point. It is thus designed such that a candidate position for the i-th point is chosen to be the position with the largest intensity gradient over the interval [−1.5, 1.5] mm along the surface normal $\hat{n}_i$. Two different approaches are used for selecting candidate positions, one for contrasted points $C \subset \{x_i\}_{i=0}^{N-1}$, which are the subset of points we know a priori are well contrasted in CT, and one for non-contrasted points $C' = \{x_i\}_{i=0}^{N-1} \setminus C$, which are the rest of the labyrinth surface points. Points that belong to C and C' have been labeled at the time the models are created. For each $x_i \in C$, a candidate position $x'_i$ is determined using Eqn. (I.2) and a reliability weight of $w_i = 0.99$ is assigned, while for each $x_i \in C'$, its original initial position determined via image registration is used as a candidate position and a reliability weight of $w_i = 0.01$ is assigned. A relatively high weight is thus assigned to the candidate positions for C so that the shape fitting is influenced more by those points with contrast in the CT. Although the results obtained with this technique are generally satisfactory, there are cases where mis-segmentation is observed. This is likely caused by the limited number of shapes used to create the ASM, which may not be able to capture enough variability to segment accurately all the images in the library. To deal with this issue, at each iteration, the final adjusted point for the i-th point is determined using the equation $$x_i^{\alpha} = \alpha \cdot x''_i + (1-\alpha) \cdot x'_i, \tag{I.9}$$

which is a weighted combination of the position of the fitted model position $x''_i$, given by Eqn. (I.4), and the candidate position $x'_i$, given by Eqn. (I.2), controlled by the weight parameter $\alpha$. We set a to be 0.8 initially and perform the iterative shape adjustment while decrementing $\alpha$ by 0.1, at the end of each iteration, for the first six iterations and use the final value of $\alpha$ for the remaining iterations. The value of $\alpha$ is set such that we largely rely on the model at the beginning. As we iteratively obtain better estimates of the shape, we gradually rely more on the candidate points which are likely to be positions with strong image gradient.

Finally, after the labyrinth is segmented algorithmically, we manually adjust the segmentation to correct for any visually identifiable error. We then rely on the segmented labyrinth surface and an ASM of the SOIs, which we previously created and reported in [2], to segment the SOIs. To do this, we first establish offline a one-to-one point correspondence between the model points of the SOIs and the model points of the labyrinth. The SOI model points are then fitted to the corresponding points on the segmented labyrinth.

Figure 7C:
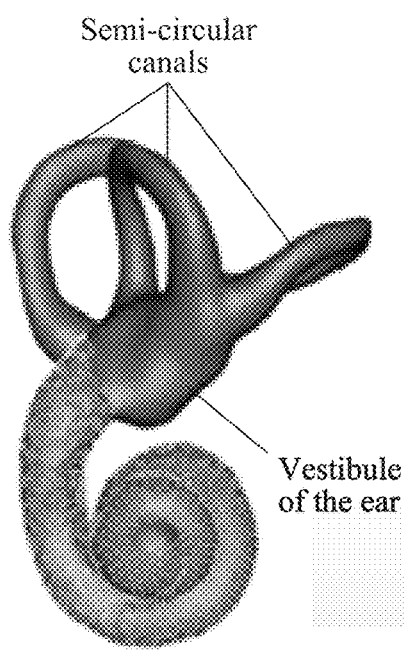
FIG. 7C shows the set of points that represent the external wall of cochlea and that are used to fit the SOI model to the labyrinth model is shown on the surface of the labyrinth.
Figure 7D:
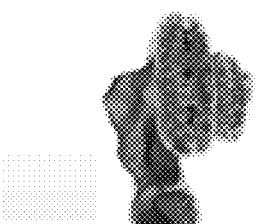
FIGS. 7D and 7E show the same set of points on the SOI surfaces.
Figure 7E:
Figure 7F:
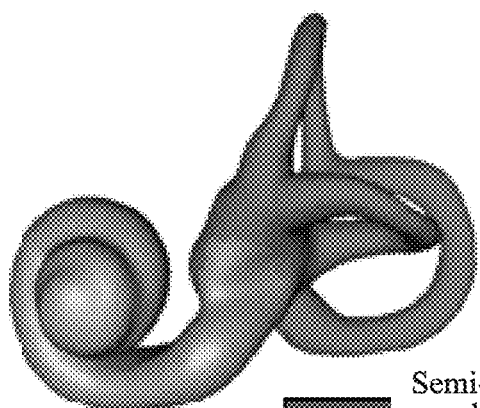
FIG. 7F shows a labyrinth surface with near points in yellow and far points in purple, according to one embodiment of the invention.

We produce the surfaces such that there is a one-to-one, across subject, point correspondence between the points composing the surfaces. For the purpose of segmentation strategy, we divide the points on each labyrinth included in the library into two groups: near points, which are points that may be close to implanted electrodes, and far points, which are the rest of points. FIG. 7F shows a surface of the labyrinth with the two point groups rendered with different colors.

I.5. Labyrinth and SOIs Segmentation

The approach for segmenting both the labyrinth and SOIs in a target CT is to first determine a coarse estimate of the structures and then refine this coarse estimate. To identify a coarse estimate of the structures, we map surfaces of the structures, chosen from the shape library, that best localize the structures in the target CT. We then create ASM models for the structures using the subset of shapes chosen, from the shape library, based on their similarity to the corresponding structure shapes in the target CT. Finally, we refine the coarse estimate using a standard weighted ASM-based segmentation method. The following subsections detail the shape library-based coarse shape estimation and the shape model-based segmentation refinement steps.

I.5.1. Shape Library-Based Segmentation Initialization

We coarsely localize the labyrinth with a labyrinth surface chosen from the shape library. The surface is chosen such that its far points, as shown in FIG. 7F, best approximate the far points portion of the labyrinth in the target CT image. This process includes several steps. First, we determine the far points of the labyrinth in the target image by fitting the far points of the labyrinth ASM (see Section I.3.1) following the segmentation process described in Section I.3.2. The far points are likely to be far from implanted electrodes. They are thus unlikely to have been affected by implant-related artifacts in the image. Next, we register each labyrinth surface in the shape library to the target image using the transformation that minimizes the RMS distance between the far points on the library surface and the far points localized in the target image in the previous step. Finally, we compute a dissimilarity quantity for each registered surface as the residual RMS. The registered surface with the smallest dissimilarity quantity $k_s$ is used as the coarse segmentation, with $k_s$ defined as $$k_s = \text{argmin}_k \left( \frac{1}{N^f} \sum_{i=0}^{N^f-1} \|x_i - T_k(x_{ki})\|^2 \right); k \in \{0, 1, \ldots, M-1\}, \quad (I.10)$$

where M is the number of subjects in the library, $\{x_i\}_{i=0}^{N^f-1}$ is the set of far points localized in the target image, $\{x_{ki}\}_{i=0}^{N^f-1}$ is the set of far points in the k-th shape in the library, $N^f$ is the number of points in the far portion of the labyrinth, and $T_k$ is the 6-DOF (three rotations, three translations) transformation that registers the two far point sets, computed as, $$T_k = \text{argmin}_T \left( \frac{1}{N^f} \sum_{i=0}^{N^f-1} \|x_i - T(x_{ki})\|^2 \right). \quad (I.11)$$

The value of the dissimilarity term is low when the shape represented by the far points localized in the target image closely matches the shape represented by the far points in the k-th surface. As shown in the results section, the far portion of the labyrinth can be used as a good landmark for predicting the position of the labyrinth. A coarse segmentation of the SOIs is obtained by projecting the $k_s$-th subject's SOI surfaces to the target image through $T_k$.

I.5.2. Shape Model-Based Segmentation Refinement

Figure 8:
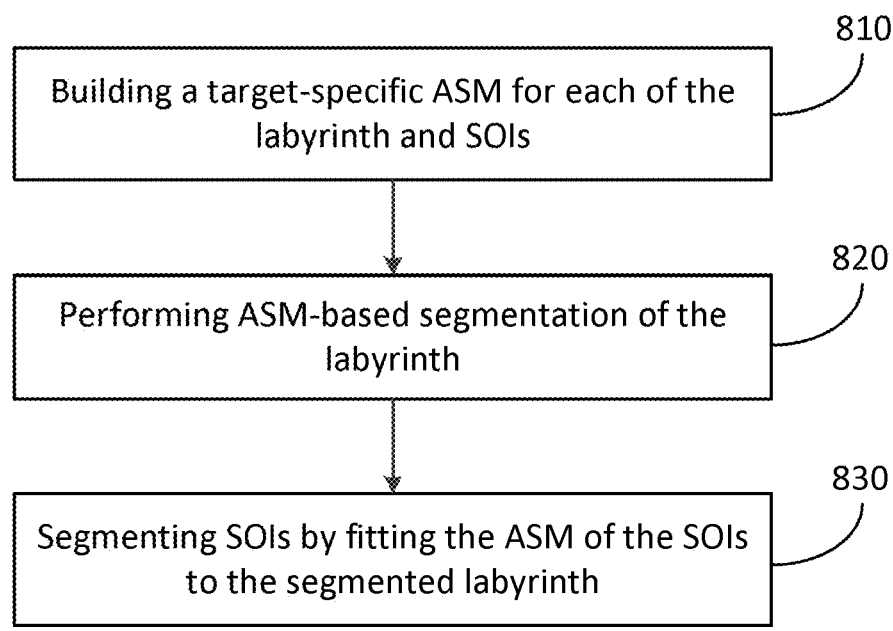
FIG. 8 shows a flowchart of a segmentation refinement process according to one embodiment of the invention.

To refine the coarse segmentations, we first segment the labyrinth by performing a weighted active shape segmentation and then segment the SOIs by fitting their ASM to the segmented labyrinth. This process is summarized in FIG. 8.

First, we create two ASMs (at step 810), one for the labyrinth and another for the SOIs using a subset of surfaces from the shape library. These are chosen as the five (a number chosen experimentally, other numbers of surfaces can also be utilized to practice the invention) surfaces with the smallest dissimilarity quantity. The ASMs created are thus specific to each target image. Next, ASM segmentation of the labyrinth is performed using the target-specific ASM (step 820), which in one embodiment includes initializing the shape; adjusting the shape and iterating the step of adjusting the shape until convergence, as discussed in Section I.3.2. Specifically, we use the coarse labyrinth localized in Section I.5.1 as the initial shape. We then iteratively refine it by first finding candidate position $x'_i$ (see Eqn. (I.2)) for each i-th point $x_i$ and then fitting the ASM to the candidate positions in a weighted least squares sense (see Eqn. (I.4)). The cost function $C_i(\cdot)$ used for candidate position selection in Eqn. (I.3) is a function of an intensity model of the image at that point. To build the intensity model, we rely on a set of manually segmented labyrinth surfaces obtained from dataset 4 of Table I. For each j-th training surface $\{x_{ji}\}_{i=0}^{N-1}$ an intensity profile $p(x_{ji})$ is extracted at each i-th point along the normal $\hat{n}_{ji}$ using the equation $$p(x_{ji}) = [I_j(x_{ji} - \Delta d \cdot 9 \cdot \hat{n}_{ji}), I_j(x_{ji} - \Delta d \cdot 8 \cdot \hat{n}_{ji}), \ldots, I_j(x_{ji} + \Delta d \cdot 9 \cdot \hat{n}_{ji})]^T, \quad (I.12)$$

where $\Delta d = 0.15$ mm, and $I_j(\cdot)$ is the intensity of the j-th training image at a given point. The intensity model at the i-th point is given by $\{p(x_{ji})\}_{j=0}^{M-1}$, where M is the number of training surfaces. Finally, the cost function is designed as $$C_i(k) = \min_j \|p(x_i + \Delta d \cdot k \cdot \hat{n}_i) - p(x_{ji})\|: j \in [0,1, \ldots, M-1]\}, \quad (I.13)$$

which defines the cost for selecting $x_i + \Delta d \cdot k \cdot \hat{n}_i$ as the candidate position for $x_i$ as the minimum Euclidean distance between the intensity profile at $x_i + \Delta d \cdot k \cdot \hat{n}_i$ and all the M intensity profiles contained in the set of model profiles at the i-th point. The reliability $w_i \in [0, 1]$ we assign for each i-th point is based on the intensity profile extracted at the i-th point in I, and is given by $$w_i = \frac{\#\{k \in \{-10, -9, \ldots, 10\}: I(x_i + \Delta d \cdot k \cdot \hat{n}_i) < R\}}{21} \quad (I.14)$$

where R is an intensity threshold that separates the bright metallic artifact from the rest of the structures. This weight is high when the set of intensity values in a given profile are below R, which indicates that the extracted profile is far from the image artifact in the image and is thus more likely to be reliable. To determine this threshold, the maxima along all the intensity profiles extracted along the surface normals at the points composing the initial shape are first computed. The threshold is then chosen experimentally to be the 90$^{th}$ percentile of the distribution of maxima. It is thus adapted to each image. Finally, at step 830, we segment the SOIs by fitting the points on the target-specific SOIs' ASM to their corresponding points on the segmented labyrinth, as discussed in Section I.4.

I.5.3. Segmentation Validation

We validate the method by automatically segmenting the ST, SV, SG and labyrinth in the post-implantation CTs in dataset 5, as listed in Table I, using the approach we propose and by measuring the resulting segmentation errors. The gold-standard surfaces that we use for comparison were created in the corresponding pre-implantation CTs by manually editing surface points on segmentations that are automatically initialized by pre-implantation CT segmentation techniques we previously developed [2, 8]. For each structure, we measure a distance from each point on its automatically generated surface to the corresponding point on its gold-standard surface, and report the mean, standard deviation, median and maximum of the distances we measure over all points on the surface. To quantify the improvement afforded by the refinement method, we measure the same segmentation error when we only use the segmentation initialization step.

I.6. Results and Discussions

Figure 9:
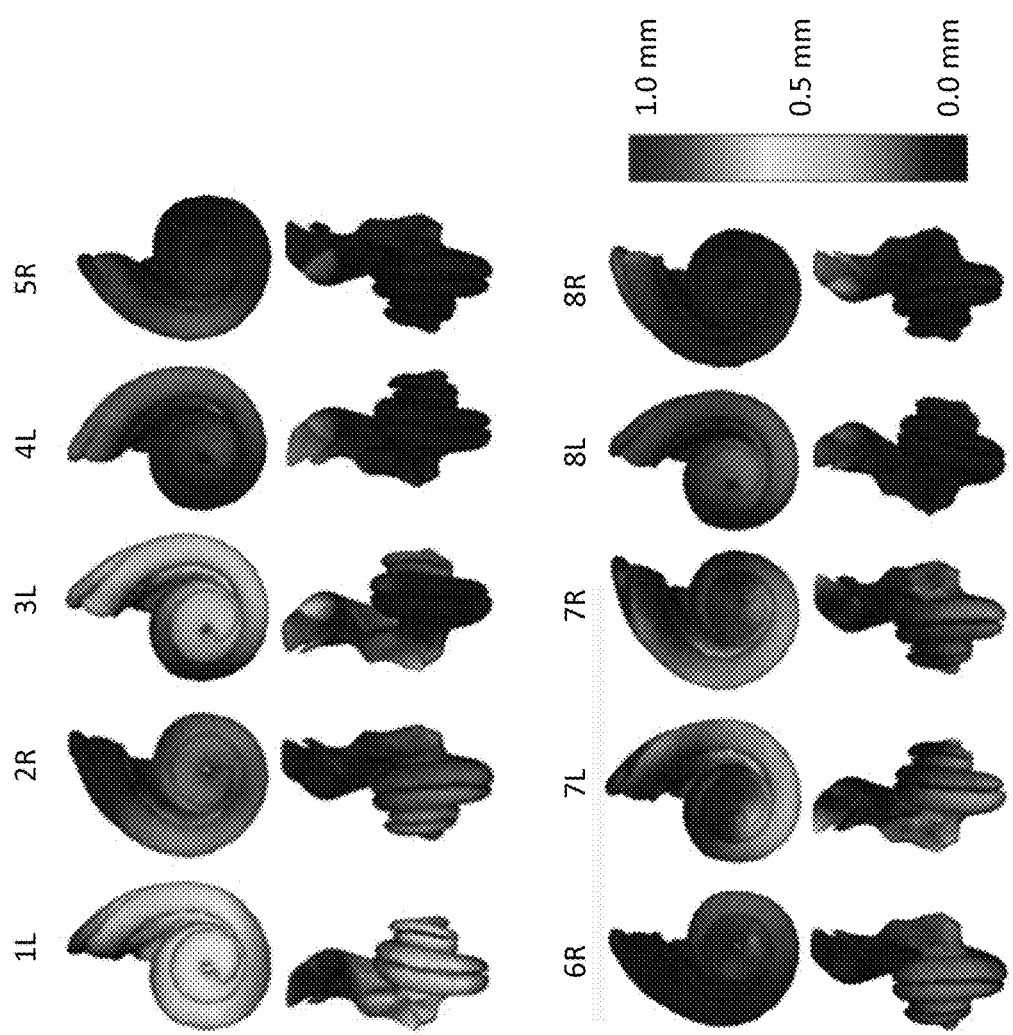
FIG. 9 shows surfaces of intra-cochlear structures color-mapped with segmentation errors viewed on the coronal plane (top row) and sagittal plane (bottom row), according to one embodiment of the invention.

Table II presents errors obtained in segmenting the entire SOIs. The mean, standard deviation, median and maximum errors are 0.254, 0.128, 0.224, 0.76 mm, respectively, for results achieved using the segmentation initialization approach alone and 0.209, 0.128, 0.181, 0.98 mm, respectively, for results achieved by refining the initial results using the segmentation refinement approach. Table III presents the same information for the labyrinth. Overall SOI average segmentation error is close to half the voxel size in the segmented CT and errors are all sub-millimetric (<1 mm). In FIG. 9, we show renderings of segmented SOI surfaces colormapped with segmentation errors for all testing ears. For the majority of the cases, SOI segmentation errors are sub-voxel, except for one (1L). For ear 1L we observed that the labyrinth surface chosen from the shape library using Eqn. (I.10) does not localize the SOIs as well as it does the far points region of the labyrinth, i.e., the relative position of the far points and the near points in this particular subject is different than in the selected library shape. This is also the case for the subset of surfaces selected to build the target-specific ASM for performing the segmentation refinement step. Because of this, the initial SOI segmentation errors are relatively large and they get worse when using the segmentation refinement step. We conducted an experiment for 1L where we perform the segmentation refinement step using an ASM built with all the shapes, rather than a subset of shapes, in the library. The final errors in segmenting the SOIs we obtain by doing so are 0.37, 0.12, 0.36, 0.78, which are smaller than the initial errors. This indicates that for ear 1L the target-specific ASM did not capture the target structure shapes well. The same phenomenon has been observed for ear 7R. However, for 80% of the test ears (8 out of 10), performing the segmentation refinement step has led to a reduction in initial segmentation errors. We do not use all shapes in the library to create the target specific ASMs because experiments we conducted show that the smallest segmentation error overall ten ears is obtained when we use target specific ASMs built with the five most similar shapes.

Figure 10:
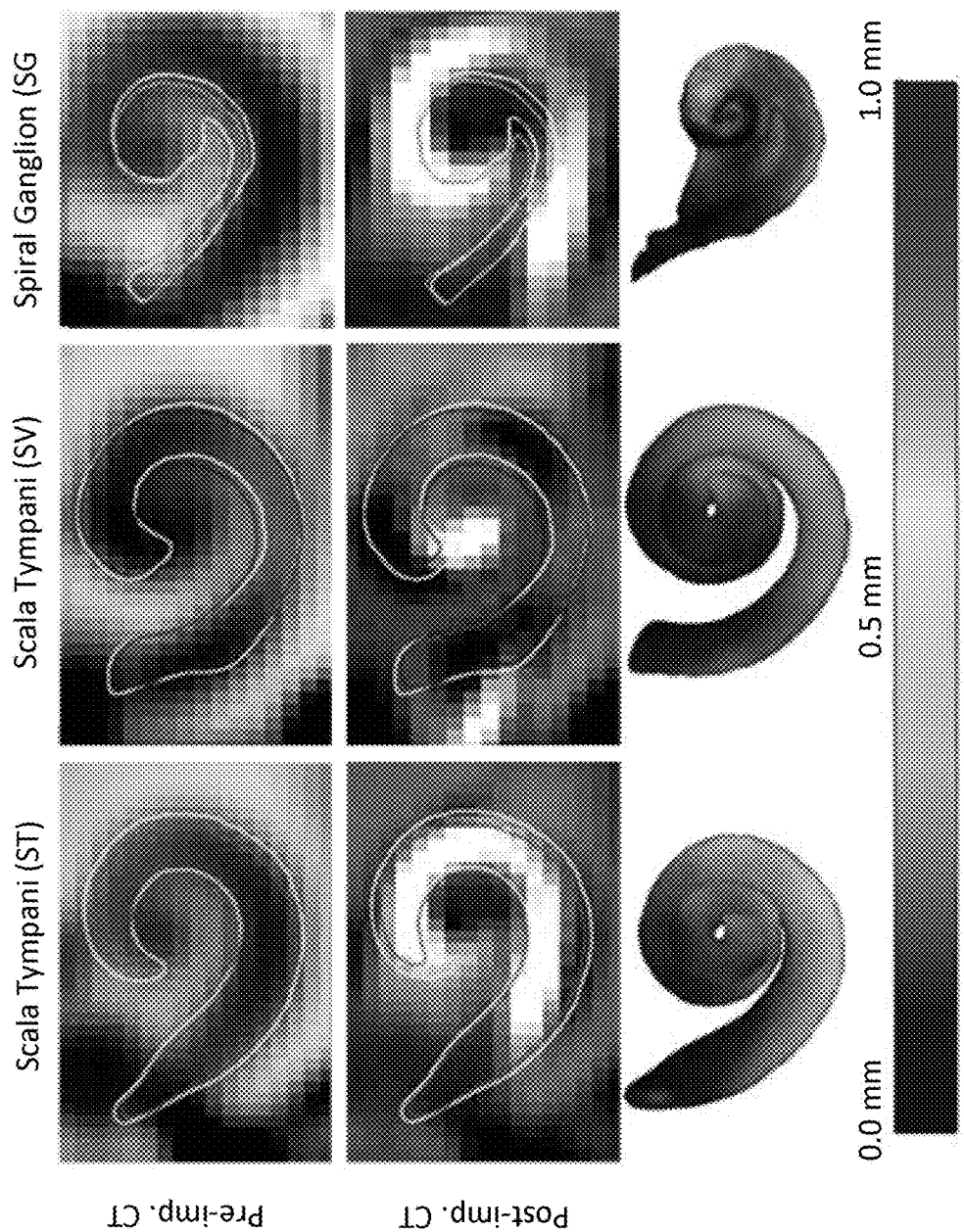
FIG. 10 shows results for a case with average error close to the overall average error according to one embodiment of the invention. The contours shown are the ST (left panel), SV (middle panel), and SG (right panel). Contours for gold-standard ST (red), SV (blue), SG (green) surfaces and contours for automatic surfaces for all structures (yellow) are shown on a slice of the pre-implantation CT (top row) and the corresponding post-implantation CT (middle row). The bottom row shows structure surfaces color-mapped with segmentation errors.

A method we previously developed for segmenting the SOIs in pre-implantation CTs [2] resulted in mean and maximum segmentation errors of 0.15 and 1.6 mm, respectively. This shows that the segmentation errors we achieve in post-implantation CTs are close to those that are achievable in pre-implantation CTs, despite the presence of metallic artifacts in the image that obscure the structures. FIG. 10 shows qualitative results for a case whose average error is close to the overall average error (7R). Both the gold-standard (yellow) and automatic (red for ST, blue for SV and green for SG) contours are overlaid on both the pre-implantation CT and the registered post-implantation CT. As can be seen in the figure, although the structures are obscured by the bright artifact introduced by the implant, there is a good agreement between the two contours along the length of the structures.

Figure 11:
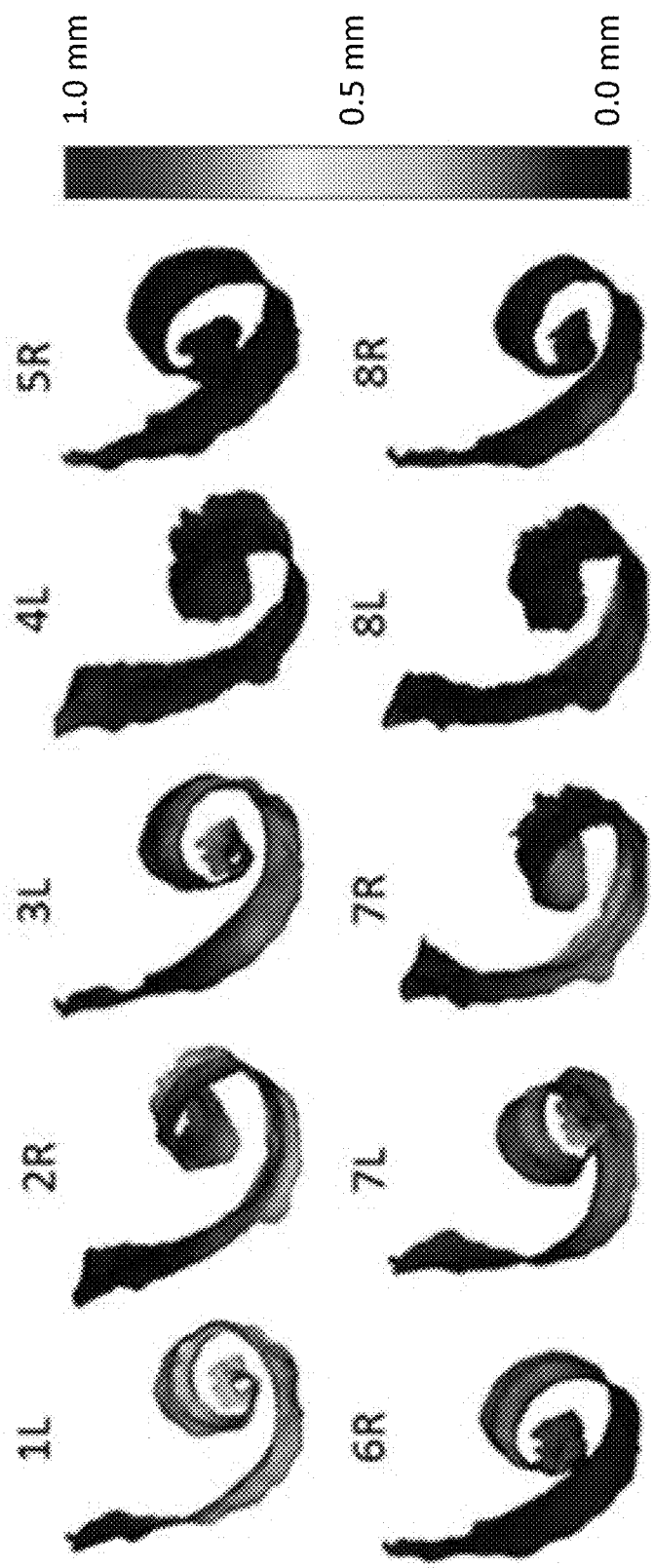
FIG. 11 shows surface of the active region color-mapped with segmentation errors for each testing ear according to one embodiment of the invention.

Table IV presents, for each testing ear, mean, standard deviation, median and maximum surface distance errors in mm for the AR, which is the part of the SOIs most likely to be stimulated by implanted electrodes and thus the most important surface for the programming application. The overall mean, standard deviation, median, and maximum errors in segmenting the AR are 0.202, 0.131, 0.169 and 0.98 mm, respectively. The corresponding errors we obtain in segmenting the AR using the segmentation initialization step alone, prior to performing the segmentation refinement step, are 0.258, 0.127, 0.225 and 0.70 mm, respectively. FIG. 11 shows renderings of the segmented AR surface for each testing ear that are color-mapped with surface distance errors in mm. As can be seen from these, errors are sub-voxel (<0.4 mm) for the majority of AR for all testing ears, except for one (1L).

TABLE II

Mean, standard deviation, median and maximum intra-cochlear anatomy (SOIs) segmentation errors in millimeters for the segmentation initialization and for the segmentation refinement steps. L is for left and R is for right ear.
Intra-cochlear anatomy

| Ear | Initial Error | | | | Final Error | | | |
|---|---|---|---|---|---|---|---|---|
|  | Mean | Std. Dev. | Median | Maximum | Mean | Std. Dev. | Median | Maximum |
| 1L | 0.39 | 0.12 | 0.40 | 0.76 | 0.44 | 0.18 | 0.44 | 0.98 |
| 2R | 0.41 | 0.11 | 0.41 | 0.72 | 0.26 | 0.05 | 0.27 | 0.39 |
| 3L | 0.27 | 0.09 | 0.26 | 0.52 | 0.24 | 0.10 | 0.23 | 0.53 |
| 4L | 0.16 | 0.07 | 0.15 | 0.38 | 0.13 | 0.05 | 0.12 | 0.31 |
| 5R | 0.18 | 0.07 | 0.17 | 0.50 | 0.13 | 0.04 | 0.13 | 0.27 |
| 6R | 0.16 | 0.06 | 0.16 | 0.37 | 0.17 | 0.06 | 0.17 | 0.31 |
| 7L | 0.35 | 0.09 | 0.35 | 0.66 | 0.25 | 0.09 | 0.25 | 0.54 |
| 7R | 0.18 | 0.06 | 0.18 | 0.35 | 0.23 | 0.08 | 0.23 | 0.50 |
| 8L | 0.15 | 0.05 | 0.15 | 0.27 | 0.14 | 0.05 | 0.14 | 0.29 |
| 8R | 0.30 | 0.09 | 0.28 | 0.54 | 0.11 | 0.05 | 0.10 | 0.33 |
| Overall | 0.254 | 0.128 | 0.224 | 0.76 | 0.209 | 0.128 | 0.181 | 0.98 |

TABLE III

Mean, standard deviation, median and maximum labyrinth anatomy segmentation errors in millimeters for the segmentation initialization and for the segmentation refinement steps
Intra-cochlear anatomy

| Ear | Initial Error | | | | Final Error | | | |
|---|---|---|---|---|---|---|---|---|
|  | Mean | Std. Dev. | Median | Maximum | Mean | Std. Dev. | Median | Maximum |
| 1L | 0.32 | 0.16 | 0.34 | 0.76 | 0.32 | 0.18 | 0.26 | 0.95 |
| 2R | 0.32 | 0.18 | 0.27 | 0.88 | 0.24 | 0.07 | 0.24 | 0.54 |
| 3L | 0.24 | 0.12 | 0.20 | 0.72 | 0.24 | 0.12 | 0.23 | 0.75 |
| 4L | 0.19 | 0.10 | 0.17 | 0.52 | 0.16 | 0.07 | 0.14 | 0.47 |
| 5R | 0.15 | 0.09 | 0.13 | 0.56 | 0.12 | 0.06 | 0.12 | 0.42 |
| 6R | 0.15 | 0.08 | 0.14 | 0.49 | 0.13 | 0.06 | 0.13 | 0.39 |
| 7L | 0.28 | 0.15 | 0.25 | 0.79 | 0.21 | 0.10 | 0.19 | 0.49 |
| 7R | 0.15 | 0.07 | 0.15 | 0.46 | 0.19 | 0.10 | 0.18 | 0.50 |
| 8L | 0.15 | 0.07 | 0.14 | 0.42 | 0.16 | 0.08 | 0.15 | 0.44 |
| 8R | 0.28 | 0.12 | 0.27 | 0.77 | 0.14 | 0.08 | 0.12 | 0.45 |
| Overall | 0.223 | 0.139 | 0.185 | 0.88 | 0.192 | 0.131 | 0.169 | 0.95 |

TABLE IV

Mean, standard deviation, median and maximum active region (AR) segmentation errors in millimeters for the segmentation initialization and for the segmentation refinement steps. L is for left and R is for right ear.
Intra-cochlear anatomy

| Ear | Initial Error | | | | Final Error | | | |
|---|---|---|---|---|---|---|---|---|
|  | Mean | Std. Dev. | Median | Maximum | Mean | Std. Dev. | Median | Maximum |
| 1L | 0.41 | 0.09 | 0.42 | 0.69 | 0.45 | 0.19 | 0.46 | 0.98 |
| 2R | 0.42 | 0.10 | 0.41 | 0.70 | 0.28 | 0.04 | 0.28 | 0.39 |

TABLE IV-continued

Mean, standard deviation, median and maximum active region (AR) segmentation errors in millimeters for the segmentation initialization and for the segmentation refinement steps. L is for left and R is for right ear.
Intra-cochlear anatomy

| | Initial Error | | | | Final Error | | | |
|---|---|---|---|---|---|---|---|---|
| Ear | Mean | Std. Dev. | Median | Maximum | Mean | Std. Dev. | Median | Maximum |
| 3L | 0.25 | 0.08 | 0.24 | 0.44 | 0.21 | 0.10 | 0.20 | 0.53 |
| 4L | 0.15 | 0.07 | 0.14 | 0.35 | 0.11 | 0.05 | 0.10 | 0.28 |
| 5R | 0.18 | 0.06 | 0.18 | 0.32 | 0.12 | 0.03 | 0.12 | 0.22 |
| 6R | 0.16 | 0.05 | 0.17 | 0.33 | 0.17 | 0.07 | 0.18 | 0.30 |
| 7L | 0.36 | 0.08 | 0.37 | 0.62 | 0.24 | 0.09 | 0.23 | 0.50 |
| 7R | 0.18 | 0.05 | 0.18 | 0.34 | 0.22 | 0.09 | 0.23 | 0.44 |
| 8L | 0.15 | 0.05 | 0.16 | 0.27 | 0.14 | 0.04 | 0.15 | 0.25 |
| 8R | 0.32 | 0.08 | 0.31 | 0.54 | 0.10 | 0.05 | 0.09 | 0.29 |
| Overall | 0.258 | 0.127 | 0.225 | 0.70 | 0.202 | 0.131 | 0.169 | 0.98 |

Briefly, the IGCIP strategies we recently developed require accurate localization of the position of implanted electrodes relative to intra-cochlear anatomy. So far, we have made this possible for subjects for whom a CT has been acquired prior to implantation, where we segment the SOIs in the pre-implantation CT, identify the electrodes in the post-implantation CT, and register the two CTs to determine the spatial relationship between the implanted electrodes and the SOIs. We have also recently presented a technique that makes IGCIP possible for subjects with no pre-implantation CT but who are implanted unilaterally. For this population of subjects, we determine the SOIs in the implanted ear using information extracted from the normal ear in the post-implantation CT. In this exemplary study, we have presented a shape library-based algorithm that does not require a pre-implantation CT of either ear to segment the SOIs.

The approach for segmentation relies on first approximating the shape of the labyrinth by mapping a labyrinth surface that is selected from a library of such surfaces, and then refining this shape by performing a weighted active shape segmentation with an ASM built to be specific for the target image. We then segment the SOIs by fitting their shape model to the external wall of the cochlea established on the segmented labyrinth. As the results we presently show, we achieve sub-millimetric errors at all points on the surfaces, and overall SOI segmentation error averages 0.209 mm. This average error is 0.202 mm for the AR, the "important" part of the SOIs. These results, which we achieve on post-implantation CTs, are comparable to those that are achievable on pre-implantation CTs and this suggests that the approach is accurate enough for use in position-based sound processing strategies. It is of note that the approach achieves this level of accuracy on an imperfect dataset composed of low-dose fpVCT images. We speculate that the approach could produce even more accurate segmentations when employed on post-implantation CTs acquired with standard CT scanners.

The segmentation results achieved using the segmentation initialization approach alone are very close to the results achieved by refining the initial results using the segmentation refinement approach. This suggests that the segmentation initialization approach alone can be used to achieve the task of segmenting the SOIs, particularly, in cases where the external wall of the cochlea in the image is completely obscured by the implant, which could prevent the segmentation refinement approach from improving the initial results. Future work will focus on exploring techniques for automatically determining when to use the segmentation initialization step alone to achieve the segmentation task.

EXAMPLE II

In this exemplary study, the method for automatic segmentation of inner ear anatomy in a post-implantation CT image is similar to that in Example I, but was applied to 25 ears, which achieves overall mean and maximum distance errors of 0.186 and 0.946 mm, respectively. The results further suggest that the method is accurate enough for extending the IGCIP strategies to all subjects.

Figure 12:
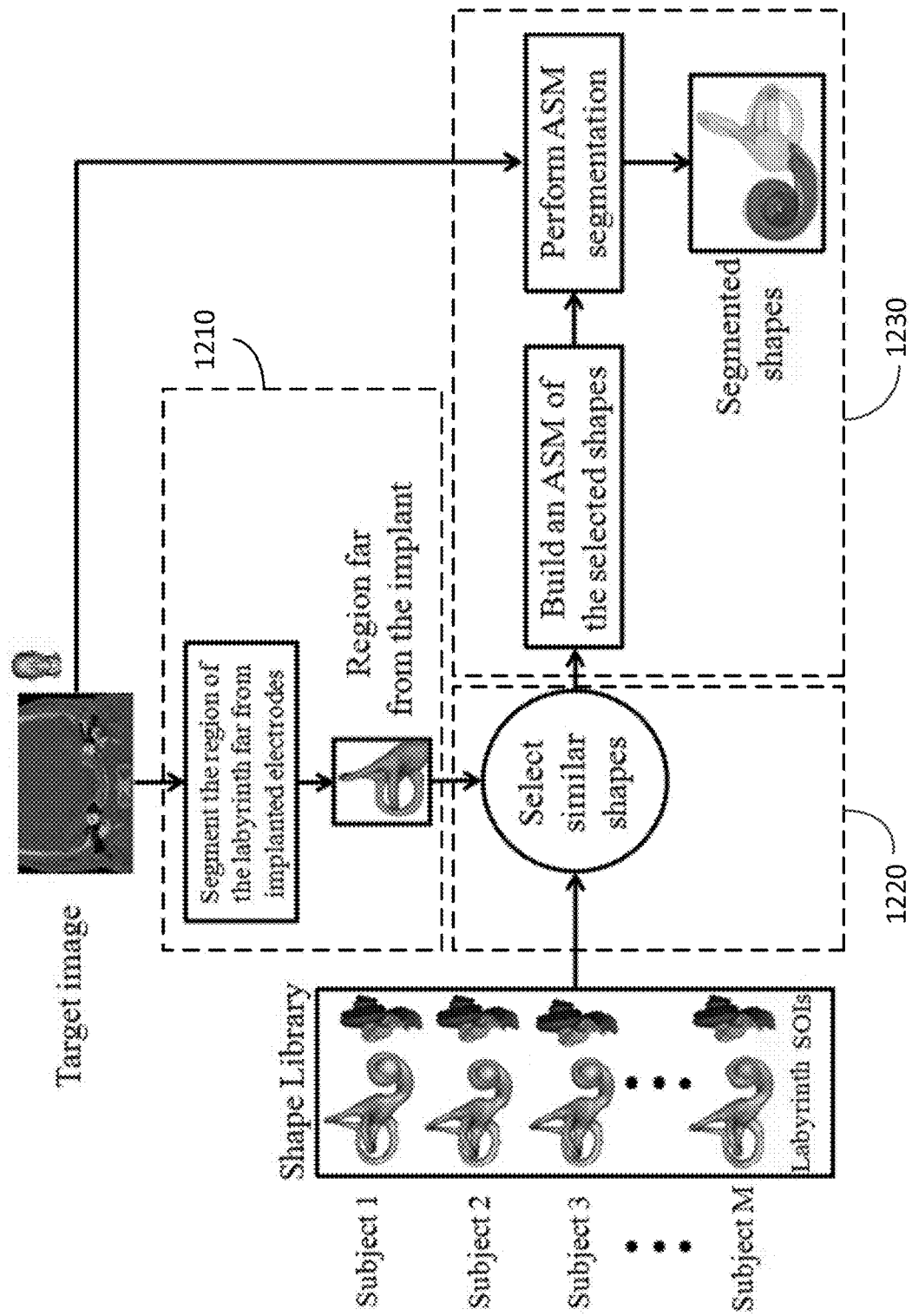
FIG. 12 shows a flow chart of inner ear anatomy segmentation according to one embodiment of the invention.

The method in one embodiment has the following steps, as shown in FIG. 12. At first, a region of the inner ear that is least likely to be affected by image artifacts is segmented at step 1210. This region is the lateral part of the labyrinth, which includes the SCCV. Next, at step 1220, the segmented SCCV's shape is used to select a set of uinner ear anatomy (the labyrinth and the SOIs) shapes from a library of inner ear anatomy shapes. The shapes are selected such that their SCCV part is nearest to the segmented SCCV based on a neighborhood criterion. Finally, the SOIs and the labyrinth are segmented by fitting statistical shape models (SSMs) of the SOIs and labyrinth built from the selected shapes at step 1230.

The labyrinth is a hollow cavity in the inner ear whose anatomical surface includes, among other anatomical surfaces, the anatomical surfaces of the semi-circular canals, the vestibule of the ear, and a part of the SOIs (the external wall of the cochlea). In this exemplary study, the surfaces of the different ear structures are constructed such that: (a) the subset of the SOI point set that represent the external wall of the cochlea is the subset of the labyrinth that represent the same, and (b) the point set of the SCCV is the subset of the labyrinth point set that represents the SSCV. FIGS. 7C-7E show for a representative subject the cochlear wall point set placed on both the labyrinth and SOI surfaces, while FIG. 7F shows the labyrinth surface with near points and far points. Thus, for each subject, there is a one-to-one point correspondence between the labyrinth, the SCCV, and the SOI point sets.

II.1. Data

The data of several groups of head CT scans used in the study are presented in Table V. The scans were acquired from several conventional scanners (GE BrightSpeed, Light-Speed Ultra; Siemens Sensation 16; and Philips Mx8000 IDT, iCT 128, and Brilliance 64) and a low-dose flat-panel volumetric CT (fpVCT) scanner (Xoran Technologies xCAT® ENT). Typical voxel size for conventional CTs is $0.25 \times 0.25 \times 0.3$ mm$^3$ and for low-dose CTs it is $0.4 \times 0.4 \times 0.4$ mm$^3$.

Low-dose fpVCT scans of 14 subjects are used for creating an intensity model of the labyrinth as discussed in section II.4, and pre- and post-implantation CT pairs of 21 subjects are used for validating the proposed segmentation algorithm as described in Section II.6. The validation dataset (dataset 3 of Table V), which includes four subgroups, is constructed such that it allows one to (1) generate automatic segmentations on the post-implantation CTs using the invented algorithm, (2) rigidly map the automatically generated segmentations onto the corresponding pre-implantation CTs, and (3) validate the mapped automatically generated segmentations by comparing them to gold-standard segmentations pre-established on the pre-implantation CTs. The first (12 subjects) comprises pairs of pre- and low-dose post-implantation CTs of 12 unilateral CI recipients. The second (2 subjects) comprises pairs of pre- and low-dose post-implantation CTs of 2 bilateral CI recipients. The third (5 subjects) comprises pairs of pre- and post-implantation CTs of 5 unilateral CI recipients. The fourth (2 subjects) comprises pairs of pre- and post-implantation CTs of 2 bilateral CI recipients. In total, we have 25 pairs of pre- and post-implantation ear CTs (12+2×2 CT-fpVCT pairs in the first and second subgroup; 5+2×2 CT-CT pairs in the third and fourth subgroup) on which we can test the invented segmentation algorithm. Each pair corresponds to one implanted ear.

In this exemplary study, the library of inner ear anatomy (the labyrinth and the SOIs) shapes was obtained from 70 subjects' CT scans, which is the same as that used in Example I. Specifically, the labyrinth and the SOIs are segmented from each subject's either left or right ear, chosen randomly. The segmentations are achieved by first automatically segmenting the respective structures using methods previously developed for the same purpose [2, 13], and then editing the automatic segmentations to correct for visually identifiable segmentation errors.

TABLE V

Datasets Used in Example II

| Data set # | Purpose | Data set Size | Acquisition Xoran fpVCT | Acquisition Conventional | CI electrodes No CIs | CI electrodes One CI | CI electrodes Two CIs |
|---|---|---|---|---|---|---|---|
| 1 | Reference (atlas) | 1 | | x | x | | |
| 2 | Intensity model creation | 14 | x | | x | | |
| 3 | Segmentation validation | 12 | | x | x | | |
| | | 2 | x | | | x | |
| | | | x | | | | x |
| | | 5 | | x | x | | |
| | | | | x | | x | |
| | | 2 | | x | x | | |
| | | | | x | | | x |

II.2. Segmentation of the SCCV

We automatically segment the SCCV using a SSM-based segmentation method previously developed for full labyrinth segmentation [14]. To build the SSM for the SCCV, we use the subset of labyrinth points from each of the 18 training labyrinth that was used to build a shape model of the full labyrinth for the previous study [14].

II.3. Selection of Nearest Neighbor (NN) Inner Ear Anatomy Shapes from a Shape Library Once the SCCV is segmented in the target image, we use it to select a set of NN inner ear anatomy (the labyrinth and the SOIs) shapes for which their SCCV shape shows high similarity with the target SCCV. This process includes the following steps.

(1) Library shape mapping: We map each library subject's labyrinth and SOI surfaces onto the target image space using the transformation that minimizes the root mean squared (RMS) distance between the library subject's SCCV points and the segmented target SCCV points.

(2) Dissimilarity quantity computation: We compute a dissimilarity quantity DS(k) for each mapped library subject k, which is defined to be the residual RMS of the registered library SCCV points, given by, $$DS(k) = \left( \frac{1}{N^f} \sum_{i=0}^{N^f-1} \|x_i - T_k(x_{ki})\|^2 \right)^{1/2} \quad (II.1)$$

where $\{x_i\}_{i=0}^{N^f-1}$ is the set of target SCCV points localized in the target image, $\{x_{ki}\}_{i=0}^{N^f-1}$ is the set of SCCV points in the k-th library shape, $N^f$ is the number of the SCCV points, and $T_k$ is the 6-DOF (three rotations, three translations) transformation that registers the two SCCV point sets, computed as, $$T_k = \operatorname{argmin}_T \left( \frac{1}{N^f} \sum_{i=0}^{N^f-1} \|x_i - T(x_{ki})\|^2 \right) \quad (II.2)$$

The value of the dissimilarity term DS(k) is low when the shape represented by the k-th library SCCV points closely matches the shape represented by the SCCV points localized on the target image. As shown in Section II.7, the SCCV is a good landmark shape for predicting the position and shape of the labyrinth and the SOIs.

(3) Selection of similar library shapes: We select a set of library shapes, $K \subset \{0, 1, \ldots, M-1\}$, where M is the size of the library, for which their dissimilarity to the target image is the smallest. The size of subset K is chosen according to the parameter selection strategy described in Section II.5. In Section II.7, we show the feasibility of predicting inner ear anatomy shapes in a target image by mapping, and selecting similar, inner ear anatomy shapes from the shape library using the SCCV as a landmark shape. Specifically, we show that (a) the choice and the minimization of the dissimilarity quantity, defined by Eqn. (II.1), is a valid strategy for selecting similar shapes from the library, and (b) the dissimilarity quantity well correlates with inner ear anatomy (labyrinth and SOIs) localization error.

II.4. SSM Segmentation of the Labyrinth and SOIs

The final step of the segmentation algorithm is to automatically create target-specific inner ear anatomy SSMs using the selected library shapes and perform a SSM-based segmentation of both the labyrinth and the SOIs.

(1) Target-specific SSM creation: Let the selected mapped library shapes for the labyrinth and the SOIs be $\{y_k\}_{k=0}^{K-1}$ and $\{x_k\}_{k=0}^{K-1}$, respectively, with $y_k=\{y_{ki}\}_{i=0}^{N-1}$ and $x_k=\{x_{ki}\}_{i=0}^{L-1}$, where K is the number of selected library shapes, N is the number of labyrinth points, and L is the number of SOI points. We use eigen-analysis to build a SSM for each shape set according to the procedure described in [12]. Thus, we have two SSMs, one for the labyrinth and another for the SOIs, built using nearest neighbor (NN) selected, as described in Section II.3. Each SSM retains the first principal eigenvectors that capture 90% of the shape variation in the respective selected NN library shapes.

Figure 13:
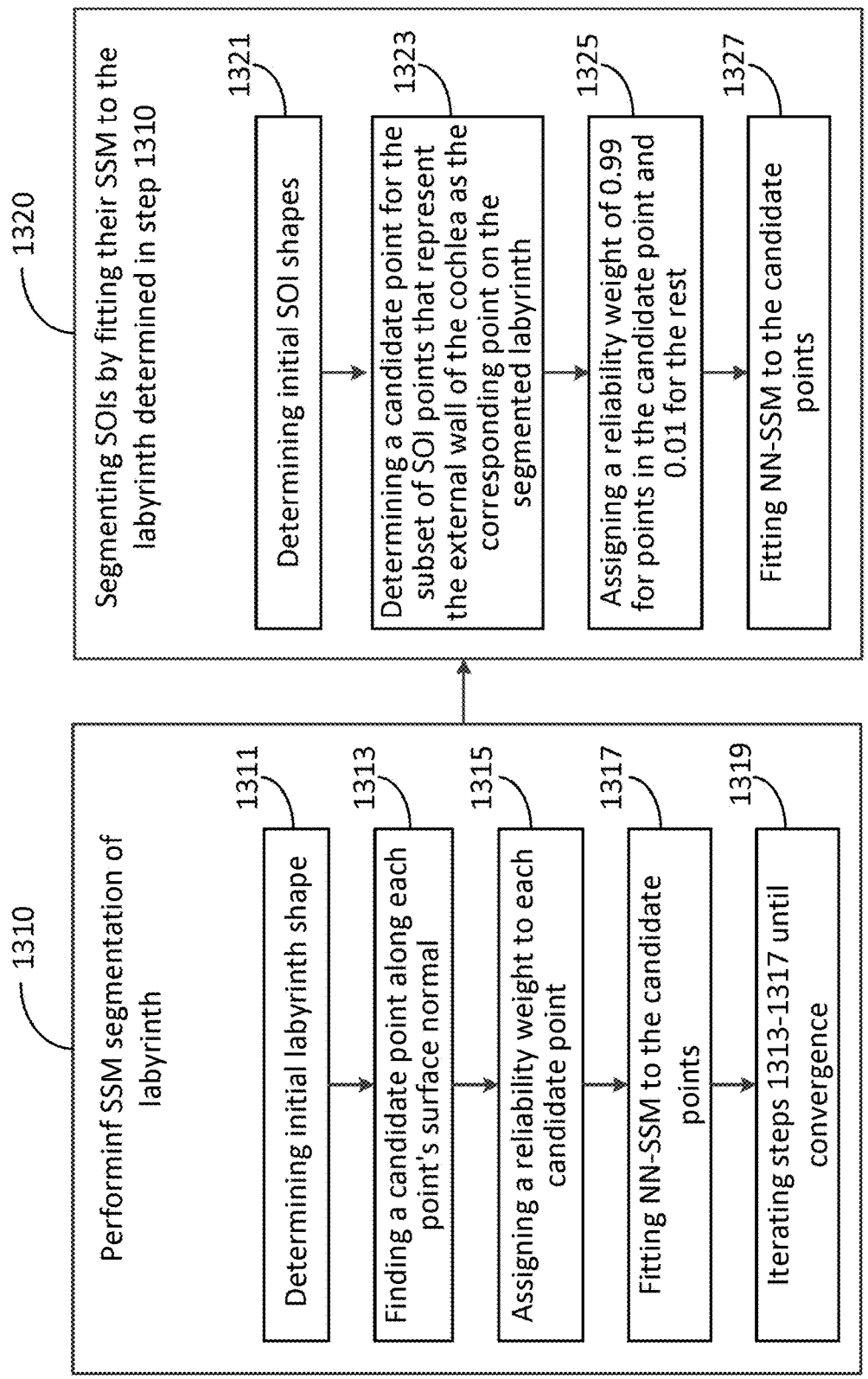
FIG. 13 shows flow charts of NN-SSM-based inner ear anatomy segmentation according to one embodiment of the invention.

(2) Target-specific SSM-based segmentation: We use the NN-SSMs to perform a SSM-based fitting to segment both the labyrinth and the SOIs. The process used to perform the SSM-based fitting is outlined in FIG. 13. In this process, we first determine the initial labyrinth shape as the labyrinth NN-SSM mean shape (step 1311). We then iteratively refine the initial shape (step 1313) by first finding a candidate position $y'_i$ for each ith point $y_i$, given by, $$y'_i = y_i + \Delta d \cdot k_{min} \cdot \hat{n}_i \quad (II.3)$$

where $\Delta d$ is a search step size, and $k_{min}$ is chosen as, $$k_{min} = \arg\max_k C_i(k) : k \in \{-10, -9, \ldots, 10\}, \quad (II.4)$$

and then fitting the NN-SSM to the candidate positions $\{y'_i\}_{i=0}^{N-1}$ in a weighted least squares sense. The cost function $C_i(\bullet)$ used for the candidate position selection in Eqn. (II.3) is tailored to the type of image to be segmented. When the target image is obtained from conventional scanners, $C_i(\bullet)$ is a function of the image gradient along the surface normal $\hat{n}_i$ at the i-th point $y_i$ in the target image I, mathematically given by, $$C_i(k)=-\|I(y_i+\Delta d(k+1)\hat{n}_i)-I(y_i+\Delta d(k-1)\hat{n}_i)\|,$$

where $\Delta d$ is set to half of the width of the voxel in I. When the target image is obtained from low-dose scanners, $C_i(\bullet)$ is a function of a 1-D intensity profile model of the image along the surface normal $\hat{n}_i$ at the ith point $y_i$ in I. To build the intensity profile model, we rely on a set of manually segmented labyrinth surfaces obtained from dataset 2 (see Table V). For each j-th training surface $\{y_{ji}\}_{i=0}^{N-1}$, an intensity profile $p(y_{ji})$ is extracted at each i-th point along the surface normal $\hat{n}_{ji}$ using the equation $$p(y_{ji})=[I_j(y_{ji}-\Delta d\cdot 10\cdot\hat{n}_{ji}), I_j(y_{ji}-\Delta d\cdot 9\cdot\hat{n}_{ji}),\ldots,I_j(y_{ji}+\Delta d\cdot 10\cdot\hat{n}_{ji})]^T, \quad (II.5)$$

where $\Delta d=0.15$ mm, and $I_j(\bullet)$ is the intensity of the j-th training image at a given point. The intensity profile model at the i-th point is given by the set $\{p(y_{ji})\}_{j=0}^{M-1}$, where M is the number of training surfaces. The cost function is then defined by the equation, $$C_i(k)=\min_j\|p(y_i+\Delta d\cdot k\cdot\hat{n}_i)-p(y_{ji})\|: j\in\{0,1,\ldots,M-1\}, \quad (II.6)$$

which defines the cost for selecting $y_i+\Delta d\cdot k\cdot\hat{n}_i$ as the minimum Euclidean distance between the intensity profile at $y_i+\Delta d\cdot k\cdot\hat{n}_i$, and the intensity profile model at the ith point. The reliability $w_i\in[0, 1]$ assigned for each ith point (step 1315) is based on intensity profile extracted at the ith point in I, and given by, $$w_i=\frac{\#\{k\in\{-10,-9,\ldots,10\}: I(x_i+\Delta d\cdot k\cdot\hat{n}_i)<R\}}{21}, \quad (II.7)$$

where R is an intensity threshold that separates the bright metallic artifact from the rest of the structures in I. This weight is high when the set of intensity values in a given profile are below R, which indicates that the extracted profile is far from the image artifact in the image and is thus more likely to be reliable. To determine this threshold, we first compute the maxima along all the intensity profiles $\{p(y_i)\}_{i=0}^{N-1}$ in I, extracted along the surface normal at $\{y_i\}_{i=0}^{N-1}$. We then choose the threshold to be the 90$^{th}$ percentile of the distribution of the maxima. The threshold R is thus adapted for each target image I. Finally, we iterate the search for candidate positions and the subsequent fitting of the NN-SSM to the candidate points until the RMS distance between fitted shape and the initial shape is less than 0.01 mm (steps 1317 and 1319). For more detail on the Fitting SSMs to candidate positions, see Section II of the inner ear anatomy segmentation study previously presented [14].

Once the labyrinth is segmented at step 1310, we use it to segment the SOIs at step 1320. First, we use the mean shape of the SOIs' NN-SSM as an initial estimate of the SOI shapes at step 1321. Next, we determine a candidate position for each point on the initial shape at step 1323. We use two different approaches to achieve this. The first approach is for contrasted SOI points (SOIs points on the external wall of the cochlea). These are the subset of SOI points that have (a) image contrast strong enough to be visually identified, and (b) a one-to-one point correspondence with the labyrinth point set. Thus, for each point in this subset, we determine a candidate position as the position of the corresponding point on the segmented labyrinth, and assign a reliability weight of $w_i=0.99$. For the remaining SOI points, which lack image contrast, we use the positions determined by the initial shape as candidate positions, and assign a reliability weight of $w_i=0.01$ for each point. At step 1325, a relatively high weight is assigned to the candidate positions for the contrasted points so that the shape fitting is influenced more by those points with contrast in image. Finally, we achieve segmentation of the SOIs by fitting their NN-SSM to the candidate positions in a weighted least squares sense at step 1327. This is a final and one-iteration fitting since the optimal candidate positions have already been determined by the labyrinth segmentation process.

II.5. Parameter Selection

Figure 14:
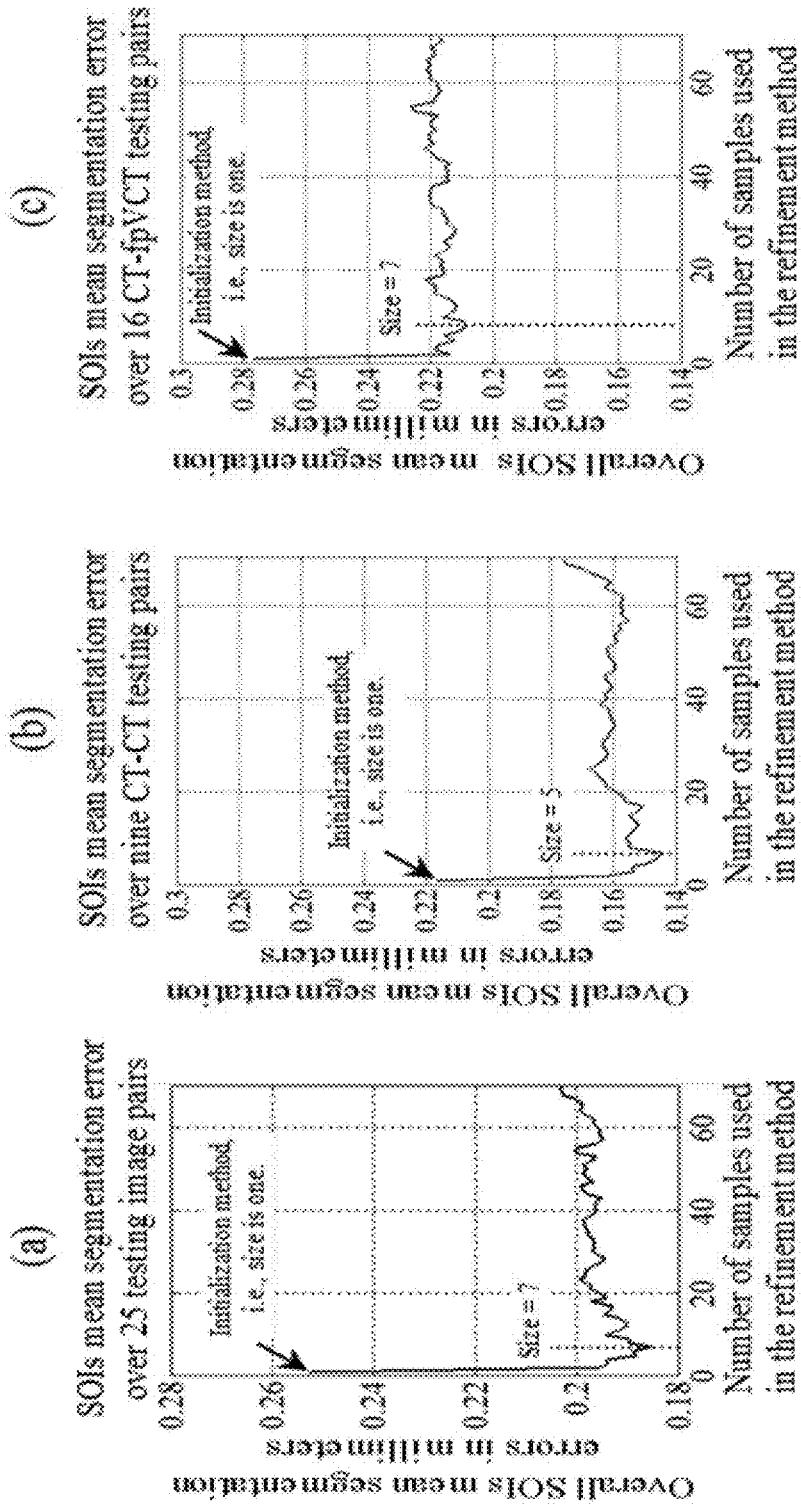
FIG. 14 shows (a) overall SOIs mean segmentation errors for all 25 testing ears versus the number of most similar shapes sampled from the shape library to create target-specific ASMs, (b) and (c) the same plot for the 9 CT-CT testing image pairs and the 16 CT-fpVCT testing image pairs, respectively, according to one embodiment of the invention.

To arrive at the size of selected NN shape subset, $K\subset\{0, 1,\ldots,M-1\}$ as described in Section II.3, we use the set of testing image pairs in dataset 3 listed in Table V. For each testing image pair, we first sort the shape library in ascending order of dissimilarity with the testing image pair, computed using Eqn. (II.1). Next, we vary the size in increments of one, from two most similar shapes to the total number of shapes in the library, and we measure the resulting SOIs mean segmentation error on all testing image pairs. This is also performed for each testing image pair. Finally, we select the size for which the SOIs mean segmentation error over all testing image pairs is the smallest. FIG. 14*a*, shows a plot of SOIs mean segmentation error over 25 testing image pairs versus the size of the selected NN library shapes, which ranges from two to 70 (the size of the shape library). As shown in the figure, the seven most similar library shapes lead to the smallest overall SOIs mean segmentation error. This is the size that is used for all testing image pairs to produce the results presented herein. FIGS. 14*b* and 14*c* shows the same plot for the 9 CT-CT testing image pairs and the 16 CT-fpVCT testing image pairs, respectively. The corresponding size for the CT-CT testing pairs is five; for the CT-fpVCT testing pairs it is seven. The first value in each plot (pointed by arrows in the figures) is the error for the SOIs segmented using one nearest shapes selected from the shape library. The plot for both groups of testing pairs suggest that (a) using more than one NN library shapes generally leads to a reduction in the overall SOIs segmentation error, and (b) using the NN-SSM-based fitting method (see Section II.D) with a subset of the library shapes, rather that all library shapes, results in smaller overall SOIs mean segmentation error.

II.6. Segmentation Validation

We validate the method by automatically segmenting the ST, the SV, the SG, the AR and the labyrinth in the post-implantation CTs in dataset 3 (see Table V) using the approach we propose and by measuring the resulting segmentation errors. The gold-standard surfaces that we use for comparison were created in the corresponding pre-implantation CTs by manually editing surface points on segmentations that are automatically initialized by pre-implantation CT segmentation techniques we previously developed [2, 8]. For each structure, we measure a distance from each point on its automatically generated surface to the corresponding point on its gold-standard surface, and report the mean, standard deviation, median and maximum of the distances we measure over all points on the surface. To quantify the improvement afforded by the refinement method, we measure the same segmentation error when we only use the segmentation initialization step.

II.7. Results and Discussions

To determine the feasibility of the initialization method, we use it to segment pre-implantation CTs for which gold-standard segmentations are available. Specifically, we relied on (a) the gold-standard segmentations of the labyrinth and SOIs established on the set of pre-implantation CTs in dataset 3 (see Table V) and (b) the shape library (see Section II.3). We then perform the following steps on each pre-implantation CT in dataset 3. First, we identify the labyrinth and SOI surfaces using the initialization method described in Section II.4.1. In this step, we use the far points of the gold-standard labyrinth established on the CT, rather than automatically determined far points. Next, we compare the identified SOI surfaces to the corresponding gold-standard SOI surfaces and measure surface distances from the points on the identified SOI surfaces to the corresponding points on the gold-standard SOI surfaces. The same distances are also measured for the labyrinth. Finally, we measure the correlation between the dissimilarity quantities, computed using Eqn. (II.1) for each shape in the library, and the errors for the SOIs localized by mapping each shape in the library.

Figure 15:
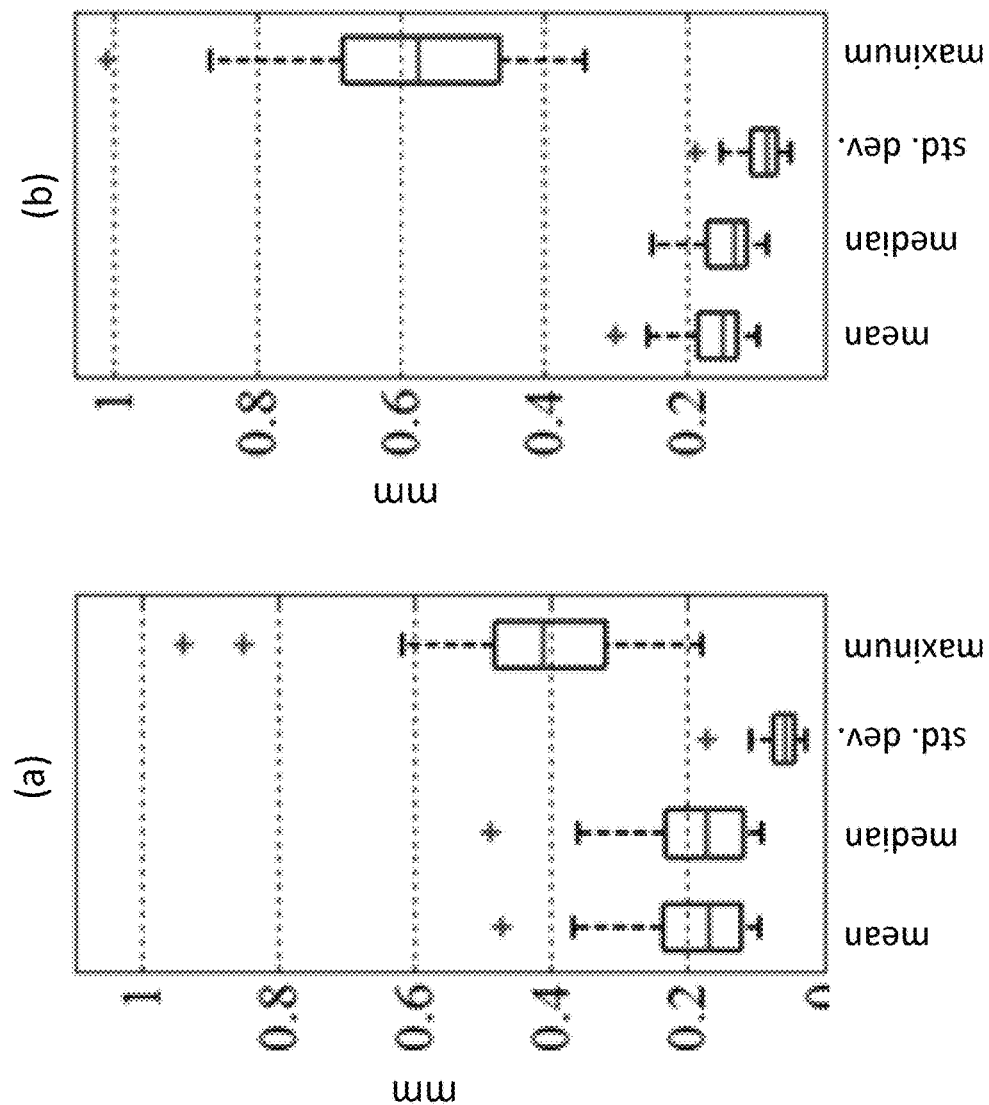
FIG. 15 shows (a) mean, median, standard deviation, and maximum distance errors box plots for the SOIs localized, on all 25 pre-implantation CTs, using the technique described in Section II.5, and (b) the same information for the labyrinth, according to one embodiment of the invention.

FIG. 15 shows the mean, median, standard deviation, and maximum error box plots for the SOIs and labyrinth localized on all 25 validation pre-implantation CTs using the segmentation initialization method as described in Section II.5. Average SOIs and labyrinth localization errors are sub-voxel. In this process, the initialization method relies on the gold-standard position of the far points, rather than automatically detected far points, for mapping the library surfaces. Thus, the results we achieve (a) are the best results that can be achieved using the initialization method, and (b) show that, given the true position of the far points, the initialization method can localize the SOIs with a sub-voxel level of accuracy.

Figure 16:
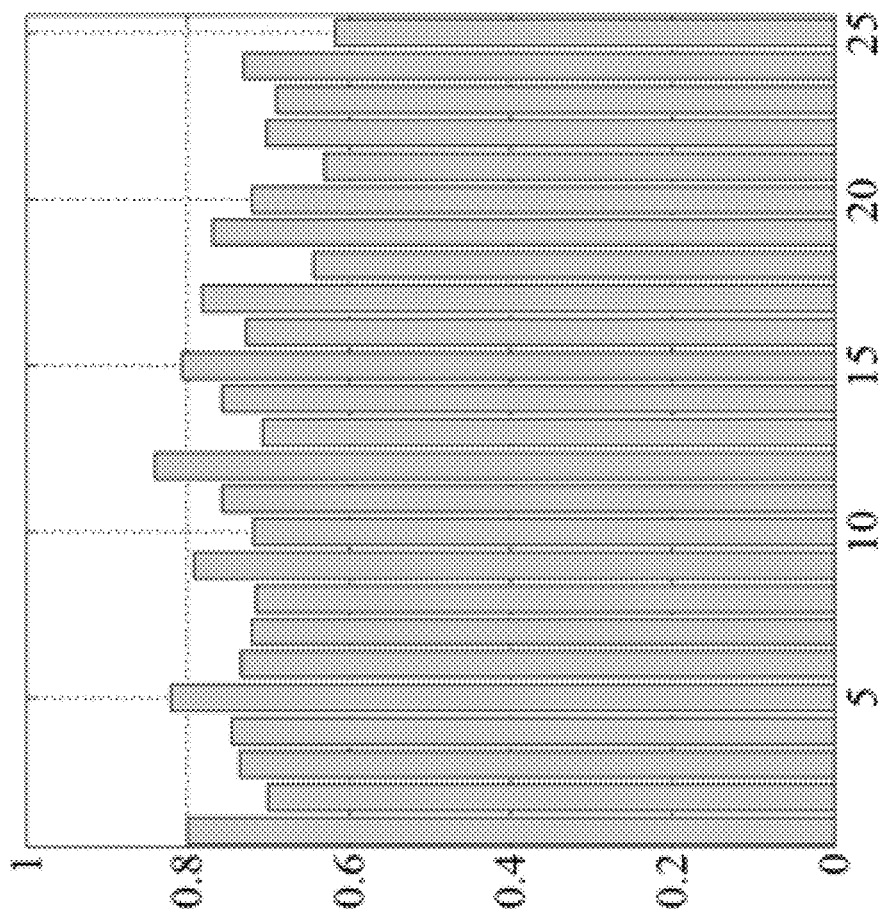
FIG. 16 shows correlation coefficient for each validation pre-implantation CT according to one embodiment of the invention.

In FIG. 16, we show bar plots for the correlation coefficients computed for all 25 validation pre-implantation CTs. For each pre-implantation CT, the correlation coefficient is computed between (a) the set of segmentation errors for the SOIs localized by mapping each shape in the library (see Section II.E), and (b) the set of dissimilarity quantities computed between the shape in that pre-implantation CT and each shape in the library. As shown in the figure, the correlation coefficient for all 25 pre-implantation CTs is in the interval [0.62, 0.84]. This result indicates that there is a good correlation between the dissimilarity quantity and the SOIs segmentation error and that the "dissimilarity" quantity we use for choosing "similar" samples in the library is a reasonably valid quantity.

Figure 17:
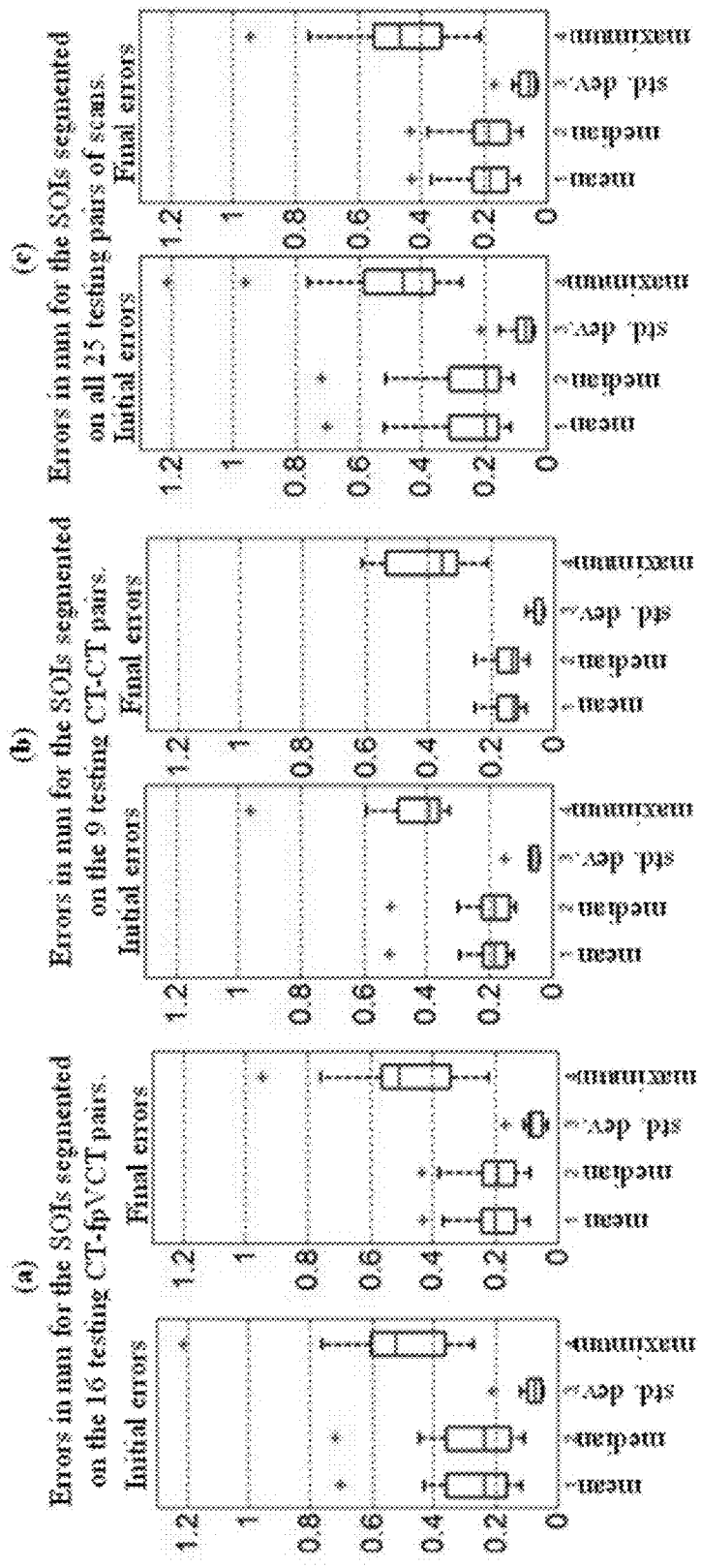
FIG. 17 shows various quantitative SOI segmentation results for test ears with low-dose post-implantation CTs (a), for test ears with conventional post-implantation CTs (b), for all 25 test ears (c), according to one embodiment of the invention. Shown for each group of test ears are (left to right), mean, median, standard deviation, and maximum error box plots for the SOIs segmented using the initialization method; mean, median, standard deviation, and maximum error box plots for the SOIs segmented using the refinement method.
Figure 18:
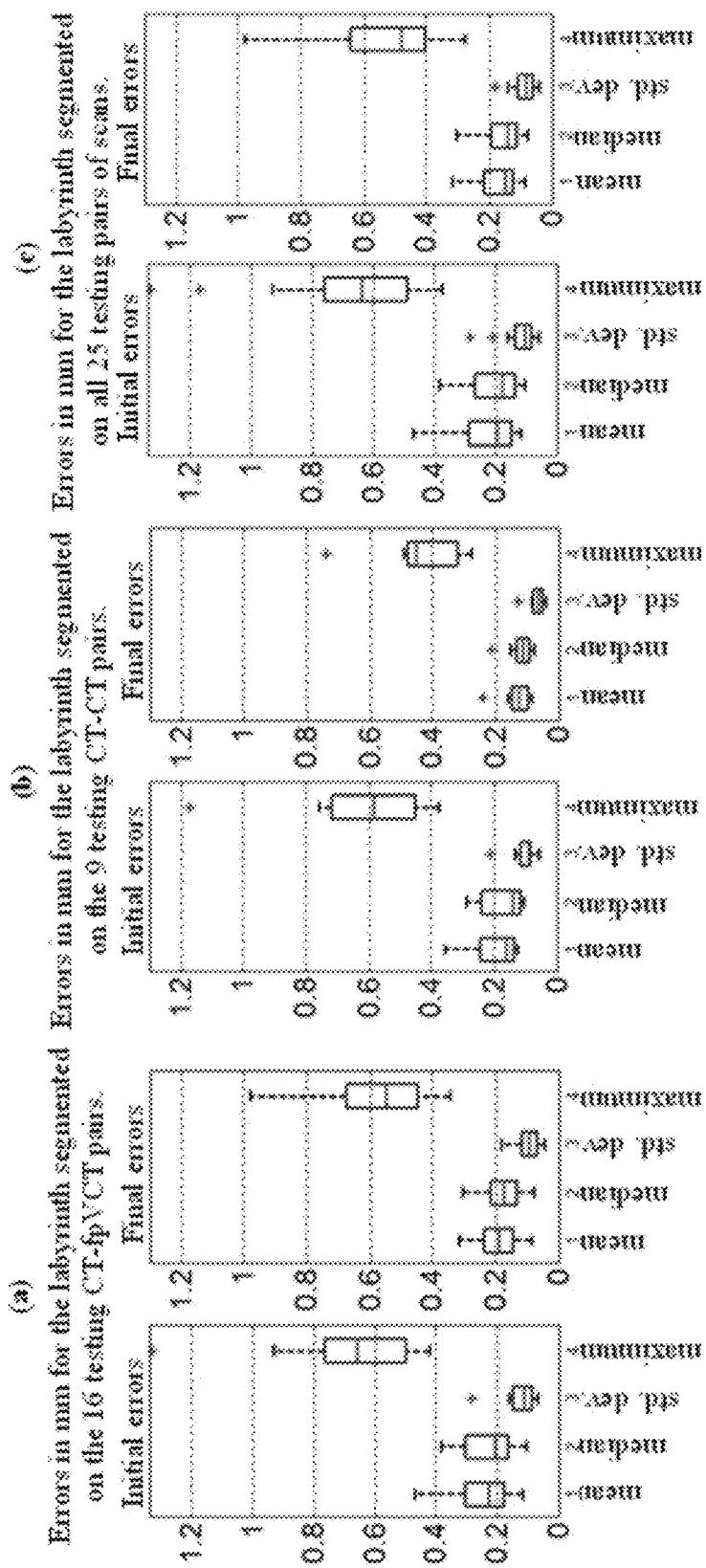
FIG. 18 shows various quantitative labyrinth segmentation results for test ears with low-dose post-implantation CTs (a), for test ears with conventional post-implantation CTs (b), for all 25 test ears (c), according to one embodiment of the invention. Shown for each group of test ears are (left to right), mean, median, standard deviation, and maximum error box plots for the labyrinth segmented using the initialization method; mean, median, standard deviation, and maximum error box plots for the SOIs segmented using the refinement method.

We evaluate the accuracy of the proposed segmentation method on the set of pre- and post-implantation testing image pairs (see dataset 4) by comparing the SOIs (the ST, the SV and the SG), the AR and the labyrinth segmentations automatically generated using the proposed method to the corresponding gold-standard segmentations established on the pre-implantation CTs. We present quantitative results for each structure generated on the 16 CT-fpVCT testing pairs, on the 9 CT-CT testing pairs, and on all 25 (16+9) testing image pairs. FIG. 18a shows the mean, standard deviation, median and maximum surface error box plots in mm for the SOIs segmented on all 16 CT-fpVCT testing pairs using the initialization method (left panel) and using the refinement method (right panel). FIGS. 17b and 17c show the same results generated on all 9 CT-CT testing pairs and on all 25 testing pairs, respectively. FIG. 18 shows the same information for the labyrinth. The results presented in FIGS. 17 and 18 show that the errors achieved on CT-CT testing pairs are smaller than those that we achieve on CT-fpVCT testing pairs. This is likely because the post-implantation CTs in the CT-CT testing pairs are of good quality, which could lead to better accuracy in structures edges localization. The overall 25 ears mean, standard deviation, median and maximum errors are 0.253, 0.162, 0.209, 1.209 mm, respectively, for results achieved using the initialization method alone and 0.186, 0.110, 0.157, 0.946 mm, respectively, for results achieved using the refinement method. Overall SOI average segmentation errors in both groups of testing pairs are close to half the voxel size in the segmented CT and are all sub-millimetric (less than 1 mm).

Figure 19:
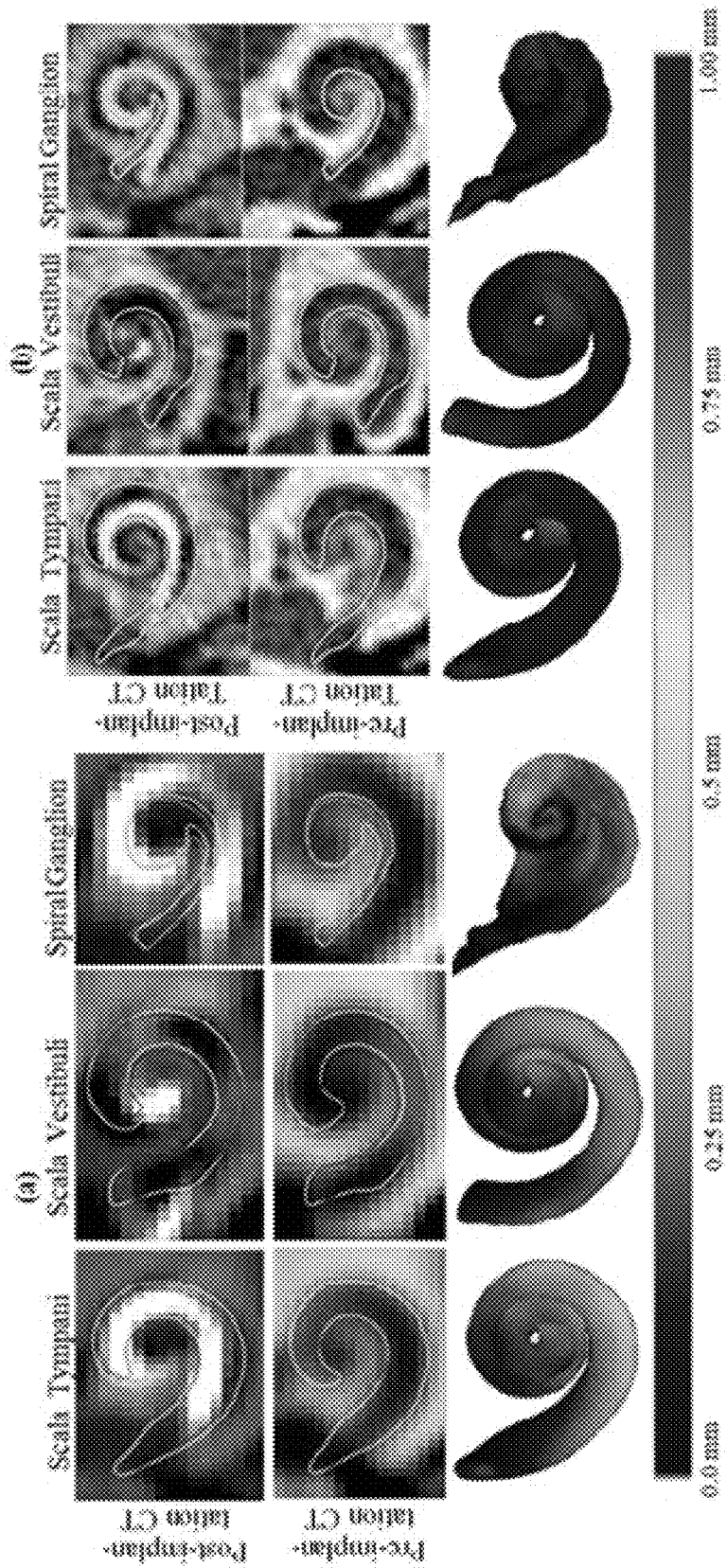
FIG. 19 shows (a) qualitative segmentation results for a testing conventional post-implantation CT with mean SOI segmentation error close to the overall mean error for the group of testing conventional CTs, where the contours shown are the ST (left panel), SV (middle panel), SG (right panel), structure contours for gold-standard ST (red), gold-standard SV (blue), gold-standard SG (green), and automatic contours for all structures (yellow) are shown in a slice of a post-implantation CT (top row) and a corresponding pre-implantation CT (middle row), on the bottom panels the structure surfaces colormapped with segmentation errors are shown, and (b) similar information for a testing Xoran post-implantation CT with mean SOI segmentation error close to the overall mean SOI segmentation error for the error close to the overall mean error for the group of testing Xoran CTs, according to one embodiment of the invention.

A method we previously developed for segmenting the SOIs in pre-implantation CTs [2] resulted in mean and maximum segmentation errors of 0.15 and 1.6 mm, respectively. This shows that the segmentation errors we achieve in post-implantation CTs are close to those that are achievable in pre-implantation CTs, despite the presence of metallic artifacts in the image that obscure the structures. FIG. 19 shows qualitative results for two ears. The left panel is for a test ear with CT-fpVCT pair (7R) whose average error is close to the overall average error in the CT-fpVCT group of testing pairs, and the right panel is for a test ear with CT-CT pair (12R) whose average error is close to the overall average error in the CT-CT group of testing pairs. Both the gold-standard (yellow) and automatic (red for ST, blue for SV and green for SG) contours are overlaid on both the pre-implantation CT and the registered post-implantation CT. As can be seen in FIG. 19, although the structures are obscured by the bright artifact introduced by the implant, there is a good agreement between the two contours along the length of the structures for both test ears.

Figure 20:
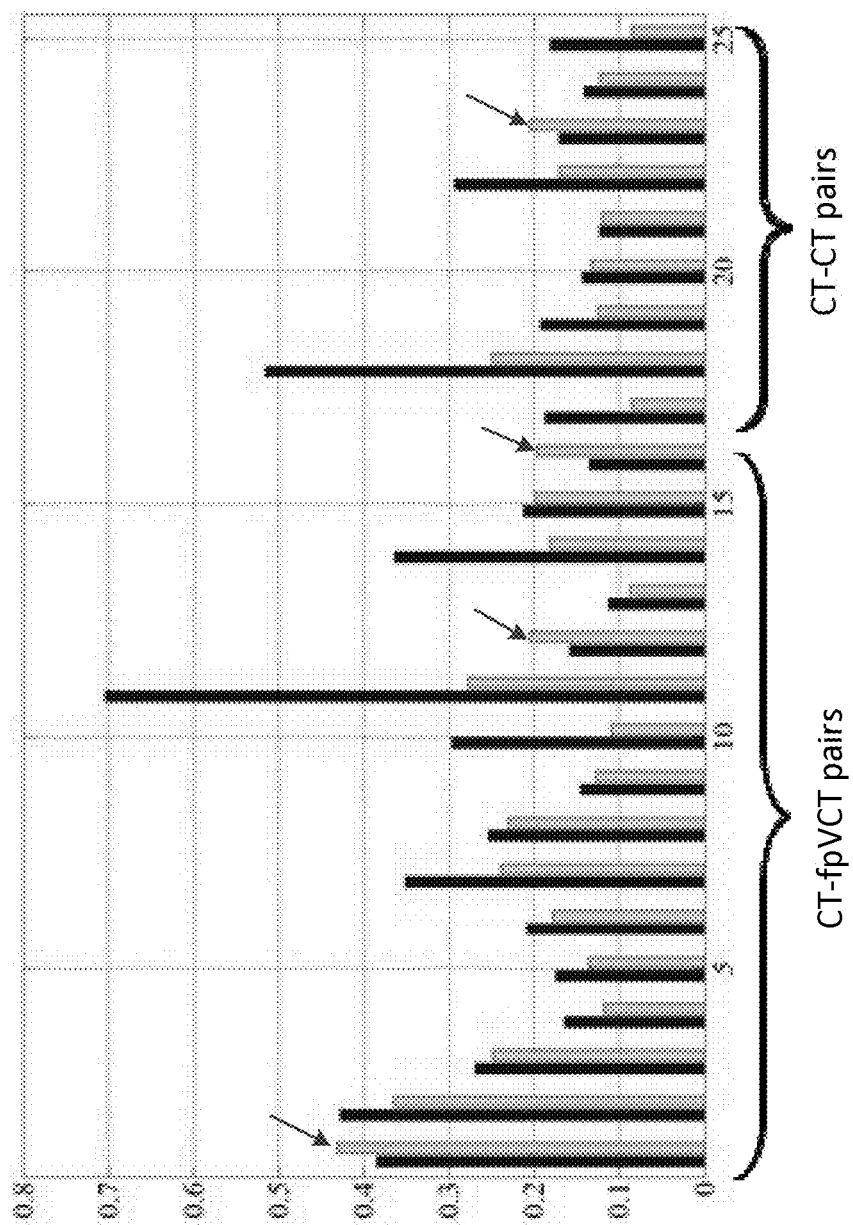
FIG. 20 shows mean error bar plots for the SOIs segmented using the initialization method alone (dark) and refinement method (light), for all 25 test ears, according to one embodiment of the invention.
Figure 21:
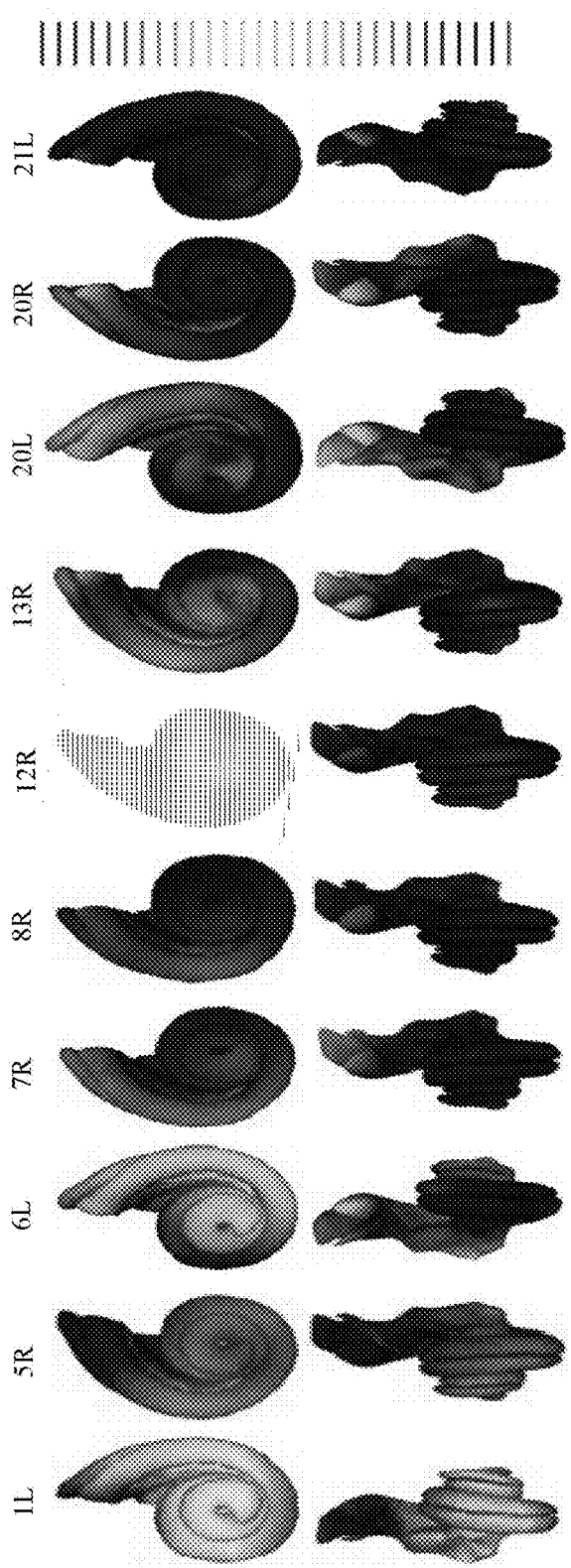
FIG. 21. Surfaces of intra-cochlear structures color-mapped with segmentation errors for representative five test ears with Xoran post-implantation CT (1L, 5R, 6L, 7R, 8R) and for representative five test ears with conventional post-implantation CT (12R, 13R, 20L, 20R, 21L), according to one embodiment of the invention.

We compared mean errors for the SOIs in each testing ear segmented using the initialization method (initial errors) and segmented using the refinement method (final errors). FIG. 20 shows bar plots for the initial mean SOIs segmentation error (dark) and final mean SOIs segmentation error (light) for each test ear. As can be shown, for the 84% of cases (21 out of 25), the refinement method has led to a reduction in initial segmentation errors. However, for the four ears (three in the CT-fpVCT testing pairs group and one in the CT-CT testing pairs group) pointed by the arrows in FIG. 20, the initial segmentation errors have gotten worse when we use the refinement method. In each of these ears, we observed that the most "similar" labyrinth shape chosen from the shape library does not localize the SOIs as well as it does the far points region of the labyrinth, i.e., the relative position of the far points and the near points in that particular subject is different than in the selected library shape. This is also the case for the subset of surfaces selected to build the target-specific ASMs for the refinement method. Because of this, the initial SOI segmentation errors are relatively large and they get worse when followed by the refinement method. We conducted experiments for the four ears where we use the refinement method with a target-specific ASM built with a larger number of most similar shapes, rather than the seven (empirically determined) most similar shapes, in the library. The final SOI segmentation errors we obtain by doing so are smaller than the initial errors for two of these ears. For the other two ears, the refinement method did not improve the initial results. This is most likely due to the image artifacts that inhibit the refinement method even when a relatively large number of shapes are used to build the target-specific ASMs. For those two ears where the refinement method reduced the initial errors, 28 and 23 shapes has been used to build the target-specific ASMs. The results from the experiment suggest that for the four ears the target-specific ASM did not capture the target structure shapes well. Although we can improve the initial segmentation errors for at least two of these ears using the refinement method with ASMs built with a larger number shapes, the results we get are not optimal overall. The cross-validation study we perform in Section II.F show that using the seven most similar shapes leads to the smallest overall SOIs mean segmentation error.

Figure 22:
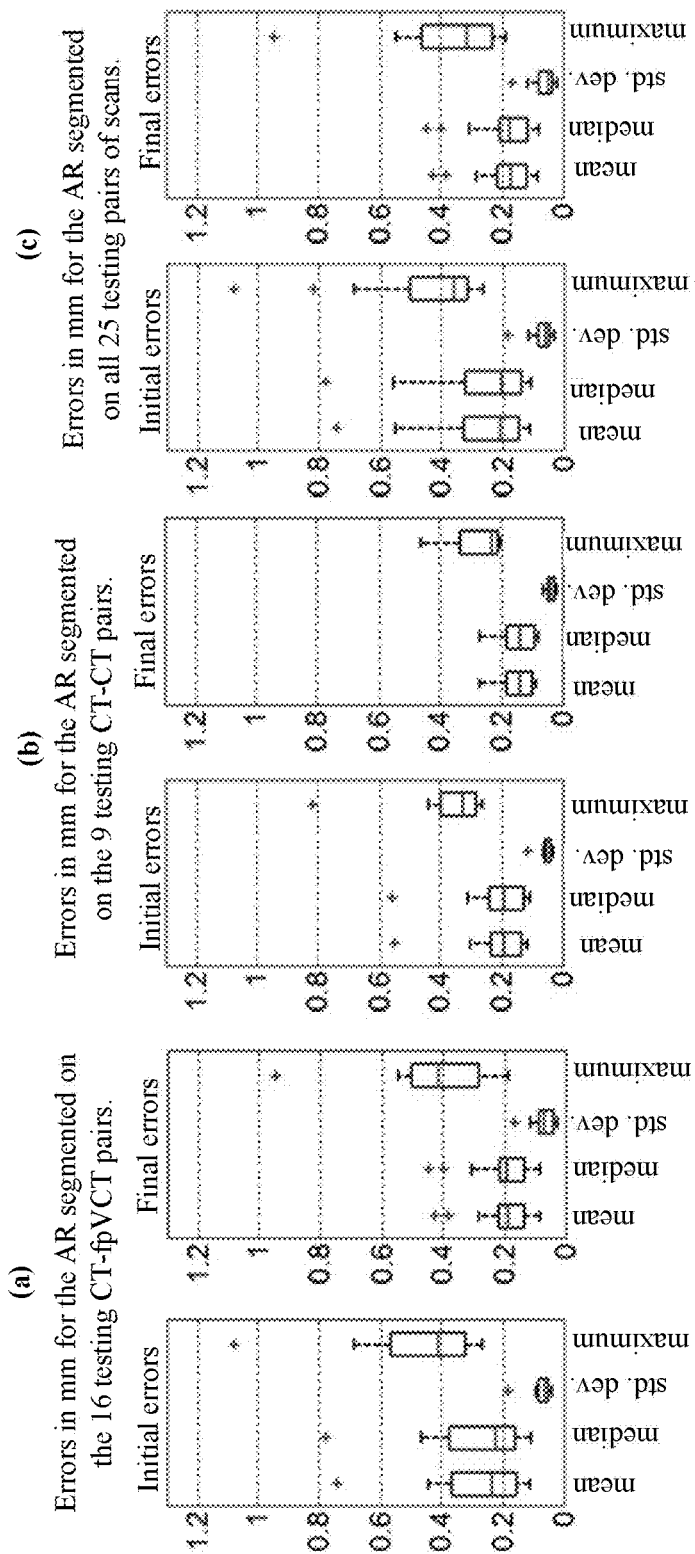
FIG. 22 shows various quantitative AR segmentation results for test ears with low-dose post-implantation CTs (a), for test ears with conventional post-implantation CTs (b), for all 25 test ears (c), according to one embodiment of the invention. Shown for each group of test ears are (left to right), mean, median, standard deviation, and maximum error box plots for the AR segmented using the initialization method; mean, median, standard deviation, and maximum error box plots for the SOIs segmented using the refinement method.
Figure 23:
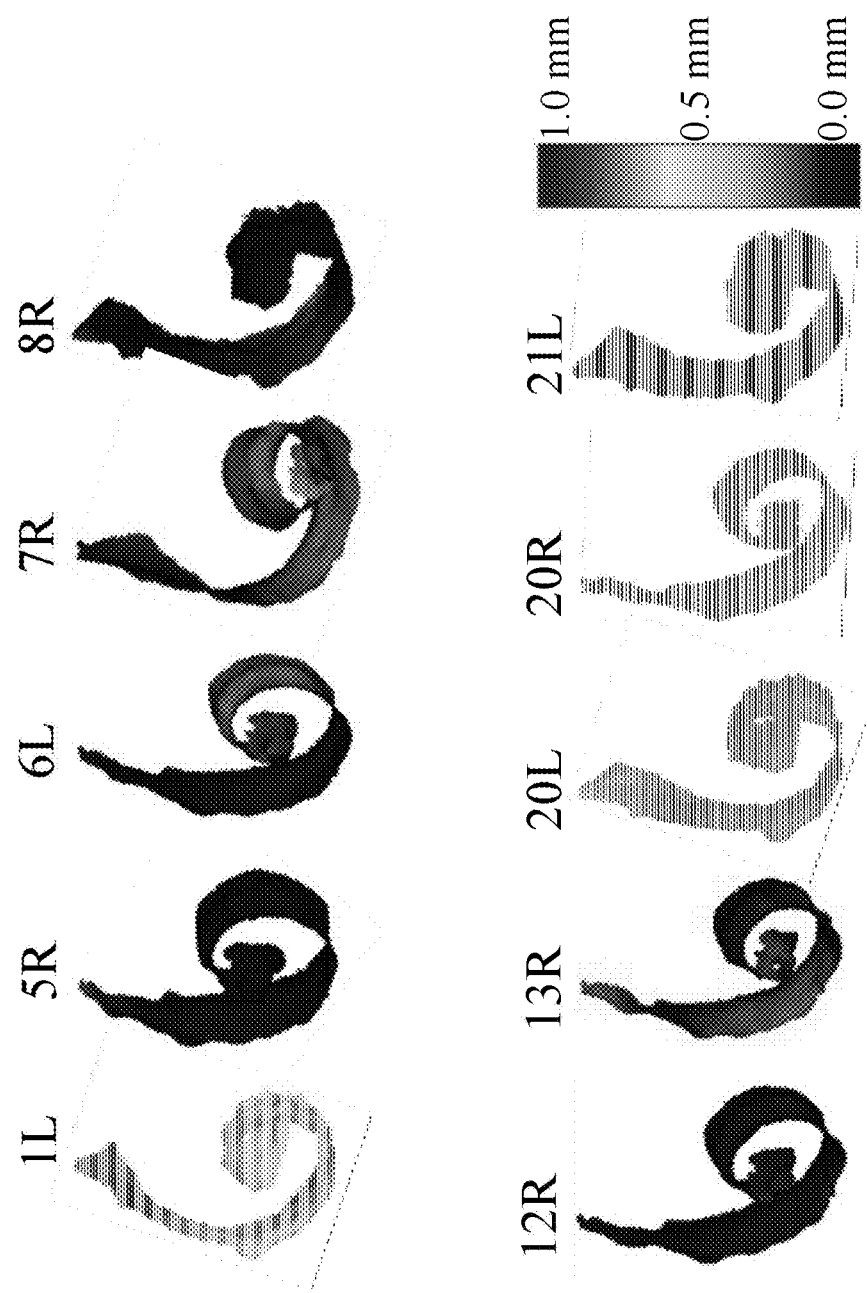
FIG. 23 shows surfaces of the active region colormapped with segmentation errors for a representative five test ears with fpVCT (1L, 5R, 6R,7R, 8L) and for a representative five test ears with conventional CTs (12R, 13R, 20L, 20R, 21L). L is for left ear and R is for right ear, according to one embodiment of the invention.

FIG. 22 presents the mean, standard deviation, median and maximum distance error box plots in mm for the AR, which is the part of the SOIs most likely to be stimulated by implanted electrodes and thus the most important surface for the programming application. The results in FIG. 22a are for the AR segmented on all 16 CT-fpVCT testing image pairs using the initialization method (left panel) and using the refinement method (right panel). FIGS. 22b and 22c show the same results on all 9 CT-CT pairs and on all 25 (16+9) testing pairs, respectively. The results in FIG. 22 show that the errors achieved on CT-CT pairs are smaller than those that we achieve on CT-fpVCT pairs. This is again likely because the post-implantation CTs in the CT-CT testing pairs are of good quality, which could lead to better accuracy in structure edges localization. The overall mean, standard deviation, median, and maximum errors in segmenting the AR on all 25 testing ears are 0.181, 0.108, 0.153 and 0.946 mm, respectively. The corresponding errors we obtain in segmenting the AR using the initialization method alone, prior to performing the refinement method, are 0.256, 0.167, 0.209 and 1.079 mm, respectively. FIG. 23 shows renderings of segmented AR surface for 10 representative ears (five with CT-fpVCT pairs and another five with CT-CT pairs) colormapped with the final errors in mm. As can be seen from these, errors are sub-voxel (<0.4 mm) for the majority of AR for all representative ears, except for one (1L).

The IGCIP strategies we recently developed and are currently testing require accurate localization of the position of implanted electrodes relative to inner ear anatomy. So far, we have made this possible for subjects for whom a CT has been acquired prior to implantation, where we segment the SOIs in the pre-implantation CT, identify the electrodes in the post-implantation CT, and register the two CTs to determine the spatial relationship between the implanted electrodes and the SOIs. We have also recently presented a technique that make IGCIP possible for subjects with no pre-implantation CT but who are implanted unilaterally. For this population of subjects, we determine the SOIs in the implanted ear using information extracted from the contralateral normal ear in the post-implantation CT. In this study, we have presented a shape library-based algorithm that does not require a pre-implantation CT of either ear to segment the SOIs.

The approach for segmentation relies on first approximating the shape of the labyrinth by mapping a labyrinth surface that is selected from a library of such surfaces, and then refining this shape by performing a weighted active shape segmentation with an ASM built to be specific for the target image. We then segment the SOIs by fitting their shape model to the external wall of the cochlea established on the segmented labyrinth. As the results we present show, we achieve sub-millimetric errors at all points on the surfaces, and overall SOIs segmentation error averages 0.144 mm over nine conventional post-implantation CTs, 0.209 mm over 16 low-dose post-implantation CTs, and 0.186 mm overall 25 post-implantation CTs. These are 0.146, 0.200, and 0.181 mm for the AR, the "important" part of the SOIs. These results, which we achieve on post-implantation CTs, are comparable to those results that are achievable on pre-implantation CTs and this indicates that the approach is accurate enough for use in position-based sound processing strategies. The approach shows superior accuracy when employed on conventional CTs than on low-dose CTs. It is of note that the method can also be employed to segment SOIs on pre-implantation CTs.

The feasibility study we perform suggests that the initialization method is a feasible method for segmenting the inner ear structures. The segmentation results we achieve using the initialization method alone are very close to those results we achieve by refining the initial results using the refinement method. This shows that the initialization method alone can be used to achieve the task of segmenting the SOIs, particularly, in cases where the external wall of the cochlea in the image is completely obscured by the implant, which could prevent the refinement method from improving the initial results.

Future work will focus on exploring techniques for automatically determining when to use the initialization method alone to achieve the segmentation task. Future work will also include using the proposed segmentation method for determining electrode position-dependent programming strategies for CI users initially at the institution and, subsequently, at other institutions.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

LIST OF REFERENCES

[1]. Noble, J. H., Labadie, R. F., Gifford, R. H., Dawant, B. M., "Image-guidance enables new methods for customizing cochlear implant stimulation strategies," Neural Systems and Rehabilitation Engineering, IEEE Transactions on 21(5):820-829, September 2013.

[2]. Noble, J. H., Labadie, R. F., Majdani, O., Dawant, B. M., "Automatic Segmentation of Intracochlear Anatomy in Conventional CT," Biomedical Engineering, IEEE Transactions on, 58(9):2625-2632, September 2011.

[3]. Noble, J. H., Schuman, T. A., Wright, C. G., Labadie, R. F., Dawant, B. M., "Automatic identification of cochlear implant electrode arrays for post-operative assessment", Proc. SPIE 7962, Medical Imaging 2011: Image Processing, 796217.

[4]. Schuman, T. A., Noble, J. H., Wright, C. G., Wanna, G. B., Dawant, B. M., Labadie, R. F., "Anatomic Verification of a Novel, Non-rigid Registration Method for Precise Intrascalar Localization of Cochlear Implant Electrodes in Adult Human Temporal Bones Using Clinically-available Computerized Tomography," The Laryngoscope, 120 (11): 2277-2283, 2010.

[5]. Wanna, G. B., Noble, J. H., McRackan, T. R., Dawant, B. M., Dietrich, M. S., Watkins, L. D., Rivas, A., Schuman, T. A., Labadie, R. F., "Assessment of electrode positions and audiological outcomes in bilateral cochlear implant patients," *Otology & Neurotology,* 32(3):428-432, 2011.

[6]. Noble, J. H., Gifford, R. H., Labadie, R. F., Dawant, B. M., "Statistical Shape Model Segmentation and Frequency Mapping of Cochlear Implant Stimulation Targets in CT," *Medical Image Computing and Computer-Assisted Intervention—MICCAI* 2012, 421-428, 2012.

[7]. Noble, J. H., Dawant, B. M., Gifford, R. H., Labadie, R. F., "Automatic, Image-based Cochlear Implant Electrode-to-Spiral Ganglion Position Analysis: Implications for Programming," Presented at the American Otological Society, April, 2012.

[8]. Reda, F. A., Dawant, B. M., McRackan, T. R., Labadie, R. F., Noble, J. H., "Automatic segmentation of intra-cochlear anatomy in post-implantation CT", Proc. SPIE 8671, Medical Imaging 2013: Image-Guided Procedures, Robotic Interventions, and Modeling, 867101.

[9]. Maes, F., Collignon, A., Vandermeulen, D., Mrchal, G., and Suetens, P., "Multimodality image registration by maximization of mutual information," IEEE Trans. Med. Imaging 16, 187-198 (1997).

[10]. Wells III, W. M., Viola, P., Atsumi, H., Nakajima, S., Kikinis, R., "Multi-modal volume registration by maximization of mutual information," Med. Image Anal. 1, 35-51 (1996).

[11]. Rohde, G. K., Aldroubi, A., Dawant, B. M., "The adaptive bases algorithm for intensity-based nonrigid image registration," IEEE Trans. Med. Imag., vol. 22, no. 11, pp. 1470-1479, November 2003.

[12]. Cootes, T. F., Taylor, C. J., Cooper, D. H., Graham, J., "Active shape models—Their training and application," Comp. Vis. Image Understanding, vol. 61, no. 1, pp. 39-59, 1995.

[13]. Reda, F. A., Noble, J. H., Labadie, R. F., Dawant, B. M., "An artifact-robust technique for automatic segmentation of the labyrinth in post-cochlear implantation CT", Proc. SPIE 9034(9034-103), Medical Imaging 2014.

[14]. Reda, F. A., McRackan, T. R., Labadie, R. F., Dawant, B. M., Noble, J. H., "Automatic segmentation of inner ear anatomy in post-implantation CT of unilateral cochlear implant recipients", Medical Image Analysis, 18(3):605-615, April 2014.

What is claimed is:

1. A method for automatic segmentation of inner ear anatomy of a living subject in a post-implantation CT image, comprising:
coarsely segmenting a labyrinth with a labyrinth surface chosen from a library of inner ear anatomy shapes, wherein the labyrinth surface is chosen such that its far points best approximate the far points portion of the labyrinth in the post-implantation CT image;
creating a target specific active shape model (ASM) for each of the labyrinth and the structures-of-interest (SOIs) using a set of inner ear anatomy surfaces selected from the library of inner ear anatomy shapes such that the set of inner ear anatomy surfaces has the smallest dissimilarity quantity with the coarsely localized labyrinth surface in the post-implantation CT image, wherein the target specific ASM is represented by a mean shape of the structure;
refining the coarsely segmented labyrinth surface by performing an ASM-based segmentation of the labyrinth using the target-specific ASM of the labyrinth to obtain a segmented labyrinth; and
fitting points of the target-specific ASM of the SOIs to their corresponding points on the segmented labyrinth to segment the SOIs in the post-implantation CT image.

2. The method of claim 1, further comprising, prior to fitting the points of the target-specific ASM of the SOIs to their corresponding points on the segmented labyrinth, establishing offline a one-to-one point correspondence between the ASM points of the SOIs and the ASM points of the labyrinth.

3. The method of claim 1, wherein the coarsely segmenting step comprises:
determining the far points of the labyrinth in the target image by performing the ASM-based segmentation and fitting the far points of the labyrinth ASM;
registering each labyrinth surface in the shape library to the target image using a transformation that minimizes the RMS distance between the far points on the library surface and the far points localized in the target image; and
computing the dissimilarity quantity for each registered surface as the residual RMS, wherein the registered surface with the smallest dissimilarity quantity is used as the coarse segmentation.

4. The method of claim 1, wherein the ASM of a structure is created by:
providing a reference surface and a set of floating surfaces of the structure with a one-to-one point correspondence between the points on the reference surface and the points on each floating surface;
registering each floating surface to the reference surface;
building a target specific ASM using the registered surfaces by an eigenanalysis method; and
storing the target specific ASM in the reference image,
wherein the set of floating surfaces comprises a set of training surfaces, or the set of inner ear anatomy surfaces selected from the library of inner ear anatomy shapes.

5. The method of claim 4, wherein the step of registering each floating surface to the reference surface is performed with a seven degrees-of-freedom (7-DOF) transformation that minimizes a root-mean-squared (RMS) distance between the training surface and the reference surface.

6. The method of claim 4, wherein the reference surface and the set of floating surfaces of the structure are provided, using a reference image and a set of floating images containing the structure, by:
segmenting the structure in the reference image to create the reference surface of the structure;
registering each floating image to the reference image to determine a corresponding registration transformation function for registering the floating image to the reference image;
segmenting the structure in each floating image by projecting the reference surface of the reference image to the floating image with the corresponding registration transformation function to generate a floating surfaces of the structure in each floating image; and
adjusting the generated floating surface of each floating image to create the set of floating surfaces of the structure.

7. The method of claim 6, wherein the step of registering each floating image to the reference image comprises:
downsampling the floating image and the reference image by a predetermined factor in each dimension;
affinely registering the floating image to the reference image;

cropping an ear region from the affinely registered floating image;
affinely registering the ear region of the floating image to an ear region of the reference image at full image resolution; and
non-rigidly registering the ear region of the floating image to the ear region of the reference image to obtain the registration transformation function.

8. The method of claim 7, wherein the predetermined factor is a factor of 1-40 in each dimension.

9. The method of claim 4, wherein the ASM-based segmentation of the structure in a target image is performed by:
(a) projecting the mean shape of the ASM of the structure from the reference image to the target image using a registration transformation that registers the two images to determine an initial shape of the structure in the target image;
(b) adjusting the initial shape of the structure by iteratively finding a candidate position for each point in the initial shape and fitting the ASM to these candidate positions in a weighted least squares sense to obtain an adjusted shape of the structure; and
(c) iterating step (b) until the RMS distance between the adjusted shape and the initial shape at that iteration is smaller than a predetermined value.

10. The method of claim 9, wherein the library of inner ear anatomy surfaces is created from a plurality of pre-implantation CT images acquired from a number of subjects, by the ASM-based segmentation of the structure in each of the plurality of pre-implantation CT images.

11. The method of claim 9, wherein each shape in the library of inner ear anatomy shapes represents the labyrinth and the SOIs of an ear.

12. The method of claim 1, wherein the SOIs comprise scala tympani (ST), scala vestibuli (SV), spiral ganglion (SG), or a combination thereof.

13. The method of claim 1, wherein the labyrinth is a structure that externally bounds the intra-cochlear anatomy and includes the semicircular canals and the vestibule (SCCV).

14. The method of claim 1, wherein the far points of the labyrinth in the post-implantation CT image are far from implanted electrodes, thereby being least likely to be affected by implant-related artifacts in the post-implantation CT image.

15. A automatic segmentation of inner ear anatomy of a living subject in a post-implantation CT image, comprising:
segmenting a region of the inner ear anatomy that is least likely to be affected by image artifacts in the post-implantation CT image so as to obtain a shape of the segmented region;
selecting a set of inner ear anatomy shapes from a library of inner ear anatomy shapes, wherein each selected inner ear anatomy shape has the smallest dissimilarity quantity with the shape of the segmented region in the post-implantation CT image, and wherein each shape in the library of inner ear anatomy shapes represents a labyrinth and structures-of-interest (SOIs) of an ear;
creating a target specific active shape model (ASM) for each of the labyrinth and the SOIs using the selected set of inner ear anatomy shapes, wherein the target specific ASM is represented by a mean shape of the structure;
performing ASM-based segmentation of the labyrinth using the target-specific ASM of the labyrinth; and
fitting points of the target-specific ASM of the SOIs to their corresponding points on the segmented labyrinth to segment the SOIs in the post-implantation CT image.

16. The method of claim 15, further comprising, prior to fitting the points of the target-specific ASM of the SOIs to their corresponding points on the segmented labyrinth, establishing offline a one-to-one point correspondence between the ASM points of the SOIs and the ASM points of the labyrinth.

17. The method of claim 15, wherein the ASM of a structure is created by:
providing a reference surface and a set of floating surfaces of the structure with a one-to-one point correspondence between the points on the reference surface and the points on each floating surface;
registering each floating surface to the reference surface;
building a target specific ASM using the registered surfaces by an eigen analysis method; and
storing the target specific ASM in the reference image,
wherein the set of floating surfaces comprises a set of training surfaces, or the set of inner ear anatomy surfaces selected from the library of inner ear anatomy shapes.

18. The method of claim 17, wherein the step of registering each floating surface to the reference surface is performed with a seven degrees-of-freedom (7-DOF) transformation that minimizes a root-mean-squared (RMS) distance between the training surface and the reference surface.

19. The method of claim 17, wherein the reference surface and the set of floating surfaces of the structure are provided, using a reference image and a set of floating images containing the structure, by:
segmenting the structure in the reference image to create the reference surface of the structure;
registering each floating image to the reference image to determine a corresponding registration transformation function for registering the floating image to the reference image;
segmenting the structure in each floating image by projecting the reference surface of the reference image to the floating image with the corresponding registration transformation function to generate a floating surfaces of the structure in each floating image; and
adjusting the generated floating surface of each floating image to create the set of floating surfaces of the structure.

20. The method of claim 19, wherein the step of registering each floating image to the reference image comprises:
downsampling the floating image and the reference image by a predetermined factor in each dimension;
affinely registering the floating image to the reference image;
cropping an ear region from the affinely registered floating image;
affinely registering the ear region of the floating image to an ear region of the reference image at full image resolution; and
non-rigidly registering the ear region of the floating image to the ear region of the reference image to obtain the registration transformation function.

21. The method of claim 20, wherein the predetermined factor is a factor of 1-40 in each dimension.

22. The method of claim 17, wherein the ASM-based segmentation of the structure in a target image is performed by:
(a) projecting the mean shape of the ASM of the structure from the reference image to the target image using a registration transformation that registers the two images to determine an initial shape of the structure in the target image;

(b) adjusting the initial shape of the structure by iteratively finding a candidate position for each point in the initial shape and fitting the ASM to these candidate positions in a weighted least squares sense to obtain an adjusted shape of the structure; and (c) iterating step (b) until the RMS distance between the adjusted shape and the initial shape at that iteration is smaller than a predetermined value.

23. The method of claim 22, wherein the library of inner ear anatomy surfaces is created from a plurality of pre-implantation CT images acquired from a number of subjects, by the ASM-based segmentation of the structure in each of the plurality of pre-implantation CT images.

24. The method of claim 15, wherein the step of fitting the target specific ASM of the SOIs to the segmented labyrinth to segmenting the SOIs comprises:

determining the mean shape of the SOIs' ASM as an initial SOI shape;

determining a candidate point for each of the subset of SOI points that represent the external wall of the cochlea in the initial SOI shape as a corresponding point on the segmented labyrinth;

assigning a first reliability weight for the candidate points and a second reliability weight for the remaining points; and fitting the SOIs' ASM to the candidate points in a weighted least squares sense.

25. The method of claim 24, wherein the first reliability weight is about 0.99, and the second reliability weight is about 0.001.

26. The method of claim 15, wherein the SOIs comprise scala tympani (ST), scala vestibuli (SV), spiral ganglion (SG), or a combination thereof.

27. The method of claim 15, wherein the labyrinth is a structure that externally bounds the intra-cochlear anatomy and includes the semicircular canals and the vestibule (SCCV).

28. The method of claim 27, wherein the step of selecting the set of inner ear anatomy shapes from the library of inner ear anatomy shapes comprises:

mapping the labyrinth and SOI surfaces of each library subject onto the post-implantation CT image using a transformation that minimizes the root mean squared (RMS) distance between the library subject's SCCV points and the segmented target SCCV points;

computing a dissimilarity quantity for each mapped library subject, wherein the dissimilarity quantity is defined to be the residual RMS of the registered library SCCV points; and selecting the set of inner ear anatomy shapes for which their dissimilarity quantity to the post-implantation CT image is the smallest.

29. A method for automatic segmentation of inner ear anatomy of a living subject in a post-implantation CT image, comprising:

segmenting a region of the inner ear anatomy as a landmark structure in the post-implantation CT image so as to obtain a shape of the segmented landmark structure; and segmenting inner ear structures of interest (SOIs) in the post-implantation CT image using the segmented landmark structure, wherein the step of segmenting the SOIs comprises:

selecting a set of inner ear anatomy shapes from the library of inner ear anatomy shapes in accordance with the shape of the segmented landmark structure, wherein each selected inner ear anatomy shape has the smallest dissimilarity quantity with the shape of the segmented landmark structure in the post-implantation CT image;

creating a target specific active shape model (ASM) for each of the landmark structure and the SOIs using the selected set of inner ear anatomy shapes, wherein the target specific ASM is represented by a mean shape of the structure;

performing ASM-based segmentation of the landmark structure using the target-specific ASM of the landmark structure; and fitting points of the target-specific ASM of the SOIs to their corresponding points on the segmented landmark structure to segment the SOIs in the post-implantation CT image.

30. The method of claim 29, wherein the region of the inner ear anatomy is in close proximity to the SOIs and is not entirely affected by image artifacts.

31. The method of claim 30, wherein the region of the inner ear anatomy is a lateral part of the labyrinth that is a structure externally bounding the intra-cochlear anatomy and includes the semicircular canals and the vestibule (SCCV).

32. The method of claim 30, wherein the step of segmenting the landmark structure comprises mapping a shape of the landmark structure chosen from a library of inner ear anatomy shapes to the post-implantation CT image, wherein each shape in the library of inner ear anatomy shapes represents the landmark structure and the SOIs of an ear.

33. The method of claim 29, further comprising, prior to fitting the points of the target-specific ASM of the SOIs to their corresponding points on the segmented landmark structure, establishing offline a one-to-one point correspondence between the ASM points of the SOIs and the ASM points of the landmark structure.

34. The method of claim 29, wherein the ASM-based segmentation of the structure in a target image is performed by:

(a) projecting the mean shape of the ASM of the structure from the reference image to the target image using a registration transformation that registers the two images to determine an initial shape of the structure in the target image;

(b) adjusting the initial shape of the structure by iteratively finding a candidate position for each point in the initial shape and fitting the ASM to these candidate positions in a weighted least squares sense to obtain an adjusted shape of the structure; and iterating step (b) until the RMS distance between the adjusted shape and the initial shape at that iteration is smaller than a predetermined value.

35. The method of claim 34, wherein the library of inner ear anatomy surfaces is created from a plurality of pre-implantation CT images acquired from a number of subjects, by the ASM-based segmentation of the structure in each of the plurality of pre-implantation CT images.

36. A non-transitory computer-readable medium storing instructions which, when executed by a processor, cause a computer or system to perform a method for automatic segmentation of inner ear anatomy of a living subject in a post-implantation CT image, the method comprising:

segmenting a region of the inner ear anatomy as a landmark structure in the post-implantation CT image so as to obtain a shape of the segmented landmark structure; and segmenting inner ear structures of interest (SOIs) in the post-implantation CT image using the segmented landmark structure, wherein the step of segmenting the SOIs comprises:

selecting a set of inner ear anatomy shapes from the library of inner ear anatomy shapes in accordance with the shape of the segmented landmark structure, wherein each selected inner ear anatomy shape has the smallest dissimilarity quantity with the shape of the segmented landmark structure in the post-implantation CT image;

creating a target specific active shape model (ASM) for each of the landmark structure and the SOIs using the selected set of inner ear anatomy shapes, wherein the target specific ASM is represented by a mean shape of the structure;

performing ASM-based segmentation of the landmark structure using the target-specific ASM of the landmark structure; and fitting the points of the target-specific ASM of the SOIs to their corresponding points on the segmented landmark structure to segment the SOIs in the post-implantation CT image.

37. The non-transitory computer-readable medium of claim 36, wherein the region of the inner ear anatomy is in close proximity to the SOIs and is not entirely affected by image artifacts.

38. The non-transitory computer-readable medium of claim 37, wherein the region of the inner ear anatomy is a lateral part of the labyrinth that is a structure externally bounding the intra-cochlear anatomy and includes the semicircular canals and the vestibule (SCCV).

39. The non-transitory computer-readable medium of claim 36, wherein the step of segmenting the landmark structure comprises mapping a shape of the landmark chosen from a library of inner ear anatomy shapes to the post-implantation CT image, wherein each shape in the library of inner ear anatomy shapes represents the landmark structure and the SOIs of an ear.

40. The non-transitory computer-readable medium of claim 36, wherein the method further comprises, prior to fitting the points of the target-specific ASM of the SOIs to their corresponding points on the segmented landmark structure, establishing offline a one-to-one point correspondence between the ASM points of the SOIs and the ASM points of the landmark structure.

41. The non-transitory computer-readable medium of claim 36, wherein the ASM-based segmentation of the structure in a target image is performed by:

(a) projecting the mean shape of the ASM of the structure from the reference image to the target image using a registration transformation that registers the two images to determine an initial shape of the structure in the target image;

(b) adjusting the initial shape of the structure by iteratively finding a candidate position for each point in the initial shape and fitting the ASM to these candidate positions in a weighted least squares sense to obtain an adjusted shape of the structure; and (c) iterating step (b) until the RMS distance between the adjusted shape and the initial shape at that iteration is smaller than a predetermined value.

42. The non-transitory computer-readable medium of claim 41, wherein the library of inner ear anatomy surfaces is created from a plurality of pre-implantation CT images acquired from a number of subjects, by the ASM-based segmentation of the structure in each of the plurality of pre-implantation CT images.

* * * * *

UNITED STATES PATENT AND TRADEMARK OFFICE
CERTIFICATE OF CORRECTION

PATENT NO. : 10,102,441 B2
APPLICATION NO. : 15/116012
DATED : October 16, 2018
INVENTOR(S) : Fitsum A. Reda et al.

It is certified that error appears in the above-identified patent and that said Letters Patent is hereby corrected as shown below:

In the Specification

Column 1, Lines 65-67 and Column 2, Lines 1-2: delete "This invention was made with government support under grant numbers R01DC008408, R21DC012620 and R01DC010184 awarded by the National Institute of Deafness and Other Communication Disorders. The government has certain rights in the invention."

And insert:
-- This invention was made with government support under grant numbers R01 DC008408, R21 DC012620, and R01 DC010184 awarded by the National Institutes of Health. The government has certain rights in the invention. --

Signed and Sealed this
Third Day of December, 2019

Andrei Iancu
*Director of the United States Patent and Trademark Office*